(12) United States Patent
Jacob et al.

(10) Patent No.: US 10,407,726 B2
(45) Date of Patent: *Sep. 10, 2019

(54) MIRNA BIOMARKERS FOR RADIATION BIODOSIMETRY

(71) Applicant: The Ohio State Innovation Foundation, Columbus, OH (US)

(72) Inventors: Naduparambil Jacob, Dublin, OH (US); Arnab Chakravarti, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/846,962

(22) Filed: Dec. 19, 2017

(65) Prior Publication Data

US 2018/0195127 A1    Jul. 12, 2018

Related U.S. Application Data

(63) Continuation of application No. 14/120,289, filed on May 14, 2014, now Pat. No. 9,890,428.

(60) Provisional application No. 61/823,063, filed on May 14, 2013.

(51) Int. Cl.
*C12Q 1/6883* (2018.01)

(52) U.S. Cl.
CPC ..... *C12Q 1/6883* (2013.01); *C12Q 2600/178* (2013.01)

(58) Field of Classification Search
None
See application file for complete search history.

(56) References Cited

PUBLICATIONS

Shah (PloS One 11(4):e0153691 pp. 1-8).*
Cui (PloS One vol. 6 No. 8 e22988 Aug. 2011).*
Dressman (PloS Medicine Apr. 2007 vol. 4 Issue 4 e106 pp. 0690-0701).*
Li (Analytical Biochemistry vol. 431 (2012) 69-75).*
Blondal (Methods vol. 59 (2013) S1-S6 Pub online Oct. 2, 2012).*
Jacob (PloS One Feb. 25, 2013 vol. 8 Issue 2 e57603 pp. 1-12).*
Chin (Singapore Med J 2007 vol. 48 No. 10 pp. 950-956).*
Waselenko (An Intern Med 2004 vol. 140 pp. 1037-1051).*
Adams BD, Guo S, Bal H, Guo Y, Megyola CM, et al. (2012) An in vivo functional screen uncovers miR-150-mediated regulation of hematopoietic injury response. Cell Rep 2:1048-1060.
Arroyo JD, Chevillet JR, Kroh EM, Ruf IK, Pritchard CC, et al. (2011) Argonaute2 complexes carry a population of circulating microRNAs independent of vesicles in human plasma. Proc Natl Acad Sci U S A 108:5003-5008.
Barcellos-Hoff MH (1998) How do tissues respond to damage at the cellular level? The role of cytokines in irradiated tissues. Radiat Res 150:S109-120.
Bartel DP (2004) MicroRNAs: genomics, biogenesis, mechanism, and function. Cell 116:281-297.
Bezman, N.A., et al., (2011) miR-150 regulates the development of NK and iNKT cells. J Exp Med. 208(13): 2717-31.
Blakely WF, Madrid JP, Sandgren DJ (2010) Biodosimetry medical recording use of the Biodosimetry Assessment Tool. Health Phys 99 Suppl 5:S184-191.
Blakely WF, Ossetrova NI, Whitnall MH, Sandgren DH, Krivokrysenko VI, et al. (2010) Multiple parameter radiation injury assessment using a nonhuman primate radiation model-biodosimetry applications. Health Phys 98:153-159.
Chang, C., et al., (1993) Characterization of the DNA double strand break repair defect in scid mice. Cancer Res. 53(6): 1244-8.
Chang WJ, Tan GB, Kuperan P (2004) Establishment of adult peripheral blood lymphocyte subset reference range for an Asian population by single-platform flow cytometry:influence of age, sex, and race and comparison with other published studies. Clin Diagn Lab Immunol 11:168-173.
Cortez MA, Bueso-Ramos C, Ferdin J, Lopez-Berestein G, Sood AK et al. (2011) MicroRNAs in body fluids—the mix of hormones and biomarkers. Nat Rev Clin Oncol 8:467-477.
Cui W, Ma J, Wang Y, Biswal S (2011) Plasma miRNA as biomarkers for assessment of total-body radiation exposure dosimetry. PLoS One 6:e22988.
Davis BN, Hilyard AC, Lagna G, Hata A (2008) SMAD proteins control DROSHA-mediated microRNA maturation. Nature 454:56-61.
DiCarlo, A.L., et al., (2011) Radiation injury after a nuclear detonation: medical consequences and the need for scarce resources allocation. Disaster Med Public Health Prep. 5 Suppl 1: S32-44.
Etheridge A, Lee I, Hood L, Galas D, Wang K (2011) Extracellular microRNA: a new source of biomarkers. Mutat Res 717:85-90.
Fevrier B, Raposo G (2004) Exosomes: endosomal-derived vesicles shipping extracellular messages. Curr Opin Cell Biol 16:415-421.
Garofalo, M., et al., (2014) The delayed pulmonary syndrome following acute high-dose irradiation:a rhesus macaque model. Health Phys. 106(1): 56-72.
Garzon, R. and C.M. Croce, (2008) MicroRNAs in normal and malignant hematopoiesis. Curr Opin Hematol. 15(4): 352-8.
Geiss GK, Bumgarner RE, Birditt B, Dahl T, Dowidar N, et al. (2008) Direct multiplexed measurement of gene expression with color-coded probe pairs. Nat Biotechnol 26:317-325.
Goans RE, Holloway EC, Berger ME, Ricks RC (1997) Early dose assessment following severe radiation accidents. Health Phys 72:513-518.
Hall EJ, Giaccia AJ (2012) Radiobiology for the Radiologist. Seventh Edition:193-200.
Hanson WR, Crouse DA, Fry RJ, Ainsworth EJ (1984) Relative biological effectiveness measurements using murine lethality and survival of intestinal and hematopoietic stem cells after fermilab neutrons compared to JANUS reactor neutrons and 60Co gamma rays. Radiat Res 100:290-297.

(Continued)

*Primary Examiner* — Amanda Haney

(74) *Attorney, Agent, or Firm* — Meunier Carlin & Curfman LLC

(57) ABSTRACT

Disclosed herein are miRNA biomarkers and methods for measuring exposure of a mammalian subject to ionizing radiation using a cell-free biological sample. Also disclosed are dosimeters and methods for triaging and treating a subject exposed to ionizing radiation.

10 Claims, 33 Drawing Sheets

(56) References Cited

PUBLICATIONS

Hassan, F., et al., (2012) MiR-101 and miR-144 regulate the expression of the CFTR chloride channel in the lung. PLoS One. 7(11): e50837.

Hunter MP, Ismail N, Zhang X, Aguda BD, Lee EJ, et al. (2008) Detection of microRNA expression in human peripheral blood microvesicles. PLoS One 3:e3694.

Iorio MV, Croce CM (2012) MicroRNA dysregulation in cancer: diagnostics, monitoring and therapeutics. A comprehensive review. EMBO Mol Med 4:143-159.

Izzotti, A., et al., (2009) Downregulation of microRNA expression in the lungs of rats exposed to cigarette smoke. Faseb J. 23(3): 806-12.

Jacob NK, Cooley JV, Yee TN, Jacob J, Alder H, Wickramasinghe P, Maclean KH, Chakravarti A. Identification of sensitive serum microRNA biomarkers for radiation biodosimetry. PLoS One. 2013;8(2):e57603.

Ji X, Takahashi R, Hiura Y, Hirokawa G, Fukushima Y, et al. (2009) Plasma miR-208 as a biomarker of myocardial injury. Clin Chem 55:1944-1949.

Jiang, X., et al., Blockade of miR-150 maturation by MLL-fusion/Myc/LIN-28 is required for MLL-associated leukemia. Cancer Cell, 2012. 22(4): 524-35.

Kosaka N, Iguchi H, Yoshioka Y, Takeshita F, Matsuki Y, et al. (2010) Secretory mechanisms and intercellular transfer of microRNAs in living cells. J Biol Chem 285:17442-17452.

Le, O.N.L, et al. (2010) Ionizing radiation-induced long-term expression of senescence markers in mice is independent of p53 and immune status. Aging Cell. 9(3):398-409.

Li C, Pei F, Zhu X, Duan DD, Zeng C (2012) Circulating microRNAs as novel and sensitive biomarkers of acute myocardial Infarction. Clin Biochem 45:727-732.

Liu Z, Zhou C, Liu Y, Wang S, Ye P, et al. (2012) The expression levels of plasma micoRNAs in atrial fibrillation patients. PLoS One 7:e44906.

Lu, L. et al., (2013) Using NanoDot dosimetry to study the RS 2000 X-ray biological irradiator. Int J Radiat Biol. 89(12): 1094-9.

MacNaughton WK (2000) Review article: new insights into the pathogenesis of radiation-induced intestinal dysfunction. Aliment Pharmacol Ther 14:523-528.

Mitchell PS, Parkin RK, Kroh EM, Fritz BR, Wyman SK, et al. (2008) Circulating microRNAs as stable blood-based markers for cancer detection. ProcNatl Acad Sci U S A 105:10513-10518.

Moses, C.T., et al., (2003) Competition for self ligands restrains homeostatic proliferation of naive CD4 T cells. Proc Natl Acad Sci U S A. 100(3):1185-90.

Oglesby, I.K., et al., (2010) miR-126 is downregulated in cystic fibrosis airway epithelial cells and regulates TOM1 expression. J Immunol. 184(4):1702-9.

Ossetrova NI, Sandgren DJ, Gallego S, Blakely WF (2010) Combined approach of hematological biomarkers and plasma protein SAA for improvement of radiation dose assessment triage in biodosimetry applications. Health Phys 98:204-208.

Prasanna, G., et al., (2010) Synopsis of partial-body radiation diagnostic biomarkers and medical management of radiation injury worksho Radiat Res. 173(2): 245-53.

Preston DL, Shimizu Y, Pierce DA, Suyama A, Mabuchi K (2003) Studies of mortality of atomic bomb survivors. Report 13: Solid cancer and noncancer disease mortality:1950-1997. Radiat Res 160:381-407.

Pritchard CC, Kroh E, Wood B, Arroyo JD, Dougherty KJ, et al. (2011) Blood cell origin of circulating microRNAs:a cautionary note for cancer biomarker studies. Cancer Prev Res (Phila) 5:492-497.

Qi P, Cheng SQ, Wang H, Li N, Chen YF, et al. (2011) Serum microRNAs as biomarkers for hepatocellular carcinoma in Chinese patients with chronic hepatitis B virus infection. PLoS One 6:e28486.

Rea, M.E., et al., (2010) Proposed triage categories for large-scale radiation incidents using high-accuracy biodosimetry methods. Health Phys. 98(2):136-44.

Rube, C.E., et al., (2000) Dose-dependent induction of transforming growth factor beta (TGF-beta) in the lung tissue of fibrosis-prone mice after thoracic irradiation. Int J Radiat Oncol Biol Phys, 47(4):1033-42.

Russo F, Di Bella S, Nigita G, Macca V, Lagana A, et al. (2012) miRandola: extracellular circulating microRNAs database. PLoS One 7:e47786.

Scholl V, Hassan R, Zalcberg IR (2012) miRNA-451:A putative predictor marker of Imatinib therapy response in chronic myeloid leukemia. Leuk Res 36:119-121.

Shimizu Y, Kodama K, Nishi N, Kasagi F, Suyama A, et al. (2010) Radiation exposure and circulatory disease risk: Hiroshima and Nagasaki atomic bomb survivor data, 1950-2003. BMJ 340:b5349.

Singh VK, Brown DS, Kao TC, seed TM (2009) Preclinical development of a bridging therapy for radiation casualties. Exp Hematol 38:61-70.

Skog J, Wurdinger T, van Rijn S, Meijer DH, Gainche L, et al. (2008) Glioblastoma microvesicles transport RNA and proteins that promote tumour growth and provide diagnostic biomarkers. Nat Cell Biol 10:1470-1476.

Teichler S, Illmer T, Roemhild J, Ovcharenko D, Stiewe T, et al. (2011) MicroRNA29a regulates the expression of the nuclear oncogene Ski. Blood 118:1899-1902.

Templin T, Amundson SA, Brenner DJ, Smilenov LB. (2011) Whole mouse blood microRNA as biomarkers for exposure to γ-rays and (56)Fe ion. Int J Radiat Biol. 87(7):653-62.

Thum T, Gross C, Fiedler J, Fischer T, Kissler S, et al. (2008) MicroRNA-21 contributes to myocardial disease by stimulating MAP kinase signalling in fibroblasts. Nature 456:980-984.

Valadi H, Ekstrom K, Bossios A, Sjostrand M, Lee JJ, et al. (2007) Exosome-mediated transfer of mRNAs and microRNAs is a novel mechanism of genetic exchange between cells. Nat Cell Biol 9:654-659.

Vasilescu C, Rossi S, Shimizu M, Tudor S, Veronese A, et al. (2009) MicroRNA fingerprints identify miR-150 as a plasma prognostic marker in patients with sepsis. PLoS One 4:e7405.

Venugopal SK, Jiang J, Kim TH, Li Y, Wang SS, et al. (2010) Liver fibrosis causes downregulation of miRNA-150 and miRNA-194 in hepatic stellate cells, and their overexpression causes decreased stellate cell activation. Am J Physiol Gastrointest Liver Physiol 298:G101-106.

Wang B, Hsu SH, Frankel W, Ghoshal K, Jacob ST (2012) Stat3-mediated activation of microRNA-23a suppresses gluconeogenesis in hepatocellular carcinoma by down-regulating glucose-6-phosphatase and peroxisome proliferator-activated receptor gamma, coactivator 1 alpha. Hepatology 56:186-197.

Waselenko JK, MacVittie TJ, Blakely WF, Pesik N, Wiley AL, et al. (2004) Medical management of the acute radiation syndrome: recommendations of the Strategic National Stockpile Radiation Working Grou Ann Intern Med 140:1037-1051.

Weiland M, Gao XH, Zhou L, Mi QS (2012) Small RNAs have a large impact: circulating microRNAs as biomarkers for human diseases. RNA Biol 9:850-859.

Xiao C, Calado DP, Galler G, Thai TH, Patterson HC, et al. (2007) MiR-150 controls B cell differentiation by targeting the transcription factor c-Myb. Cell 131:146-159.

Zernecke A, Bidzhekov K, Noels H, Shagdarsuren E, Gan L, et al. (2009) Delivery of microRNA-126 by apoptotic bodies induces CXCL12-dependent vascular protection. Sci Signal 2:ra81.

Zhang, X., et al., (2011) The ATM kinase induces microRNA biogenesis in the DNA damage response. Mol Cell. 41(4): 371-83.

Zhou B, Wang S, Mayr C, Bartel DP, Lodish HF (2007) miR-150, a microRNA expressed in mature B and T cells, blocks early B cell development when expressed prematurely. Proc Natl Acad Sci U S A 104:7080-7085.

Zhu Y, Yu X, Fu H, Wang H, Wang P, et al. (2010) MicroRNA-21 is involved in ionizing radiation-promoted liver carcinogenesis. Int J Clin Exp Med 3:211-222.

Chin (Singapore Med J 2007 vol. 48 No. 10 pp. 950-956).
Esteller (Nature Reviews Genetic vol. 12 Dec. 2011 pp. 861-874).
Wang (PloS One Jul. 2012 7(7);e41561).
Ason (PNAS Sep. 26, 2006 vol. 103 No. 39 pp. 14385-14389).
Ghorai (Frontiers in Genetics Apr. 2014 vol. 5 article 100).

* cited by examiner

| \multicolumn{3}{c}{CBA/J} | | |
| --- | --- | --- |
| Fl. COUNT IN 20μl | % | microRNA |
| 6895 | 23.10 | miR-451 |
| 3776 | 12.65 | miR-16 |
| 1179 | 3.95 | miR-21 |
| 969 | 3.25 | miR-23a |
| 923 | 3.09 | miR-22 |
| 846 | 2.83 | miR-150 |
| 678 | 2.27 | miR-25 |
| 633 | 2.12 | miR-546 |
| 553 | 1.85 | miR-223 |
| 479 | 1.60 | miR-145 |
| 388 | 1.30 | miR-720 |
| 351 | 1.18 | miR-30b |
| 334 | 1.12 | miR-29a |
| 316 | 1.06 | miR-106a+17 |
| 310 | 1.04 | miR-27a |
| 281 | 0.94 | miR-30d |
| 253 | 0.85 | let-7g |
| 248 | 0.83 | miR-205 |
| 248 | 0.83 | miR-125b-5p |
| 239 | 0.80 | miR-24 |
| 220 | 0.74 | miR-106b |
| 206 | 0.69 | miR-1902 |
| 192 | 0.64 | miR-762 |
| 191 | 0.64 | miR-130a |
| 185 | 0.62 | miR-30a |
| 180 | 0.60 | miR-20a+20b |
| 176 | 0.59 | miR-19a |
| 174 | 0.58 | miR-126-3p |
| 169 | 0.57 | miR-191 |
| 160 | 0.54 | miR-146a |
| 157 | 0.53 | miR-148a |
| 155 | 0.52 | let-7c |
| 149 | 0.50 | miR-144 |
| 146 | 0.49 | miR-571-3p |
| 131 | 0.44 | miR-203 |
| 127 | 0.42 | miR-93 |
| 120 | 0.40 | miR-122 |
| 109 | 0.36 | miR-486 |
| 106 | 0.35 | miR-126-5p |
| 104 | 0.35 | miR-29c |
| 101 | 0.34 | miR-1937a+1937b |
| 98 | 0.33 | miR-30e |
| 96 | 0.32 | miR-199a-3p |
| 93 | 0.31 | miR-2137 |
| 87 | 0.29 | let-7b |
| 86 | 0.29 | miR-19b |
| 80 | 0.27 | miR-378 |
| 79 | 0.27 | miR-222 |
| 75 | 0.25 | miR-2183 |
| 75 | 0.25 | miR-883a-3p |

*FIG. 2A*

| \multicolumn{3}{c}{C57BL/6} | | |
| --- | --- | --- |
| Fl. COUNT IN 20μl | % | microRNA |
| 8423 | 22.03 | miR-451 |
| 4718 | 12.34 | miR-16 |
| 1704 | 4.46 | miR-22 |
| 1575 | 4.12 | miR-150 |
| 1385 | 3.62 | miR-25 |
| 1359 | 3.55 | miR-21 |
| 1230 | 3.22 | miR-223 |
| 1186 | 3.10 | miR-23a |
| 1102 | 2.88 | miR-29a |
| 623 | 1.63 | miR-486 |
| 590 | 1.54 | miR-125b-5p |
| 482 | 1.26 | let-7g |
| 440 | 1.15 | miR-130a |
| 421 | 1.10 | miR-106a+17 |
| 401 | 1.05 | miR-30b |
| 386 | 1.01 | miR-191 |
| 330 | 0.86 | miR-30d |
| 326 | 0.85 | let-7c |
| 315 | 0.82 | miR-2137 |
| 307 | 0.80 | miR-126-3p |
| 299 | 0.78 | miR-720 |
| 289 | 0.76 | miR-27a |
| 271 | 0.71 | miR-145 |
| 215 | 0.56 | miR-148a |
| 209 | 0.55 | miR-19a |
| 204 | 0.53 | miR-328 |
| 204 | 0.53 | miR-146a |
| 202 | 0.53 | let-7b |
| 200 | 0.52 | miR-378 |
| 197 | 0.51 | miR-20a+20b |
| 185 | 0.48 | miR-30a |
| 176 | 0.46 | miR-24 |
| 173 | 0.45 | miR-762 |
| 157 | 0.41 | miR-122 |
| 155 | 0.40 | miR-1902 |
| 143 | 0.37 | miR-106b |
| 135 | 0.35 | miR-29c |
| 133 | 0.35 | miR-342-3p |
| 123 | 0.32 | miR-199a-3p |
| 122 | 0.32 | miR-205 |
| 114 | 0.30 | miR-93 |
| 110 | 0.29 | miR-574-3p |
| 100 | 0.26 | miR-125a-5p |
| 100 | 0.26 | miR-19b |
| 98 | 0.26 | miR-2133 |
| 97 | 0.25 | miR-350 |
| 91 | 0.24 | miR-140 |
| 91 | 0.24 | miR-126-5p |
| 91 | 0.24 | miR-669f |
| 89 | 0.23 | miR-709 |

*FIG. 2B*

| RHESUS MONKEY |
|---|
| miRNA |
| miR-451a |
| miR-223-3p |
| miR-16-5p |
| miR-142-3p |
| miR-126-3p |
| miR-25-3p |
| miR-150-5p |
| miR-1283 |
| let-7g-5p |
| let-7a-5p |
| miR-23a-3p |
| miR-191-5p |
| miR-15b-5p |
| miR-148a-3p |
| miR-93-5p |
| miR-15a-5p |
| miR-520f |
| miR-4454 |
| miR-21-5p |

*FIG. 2C*

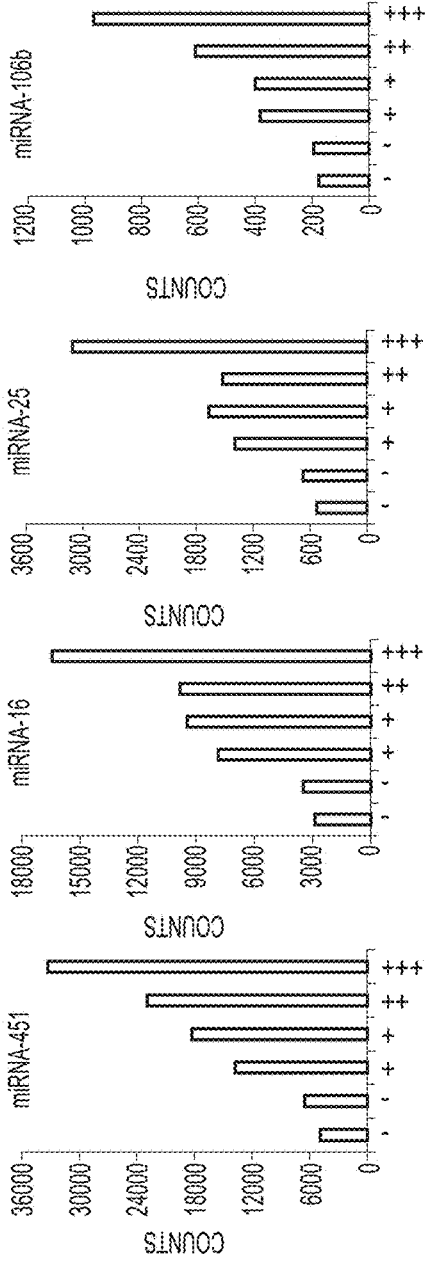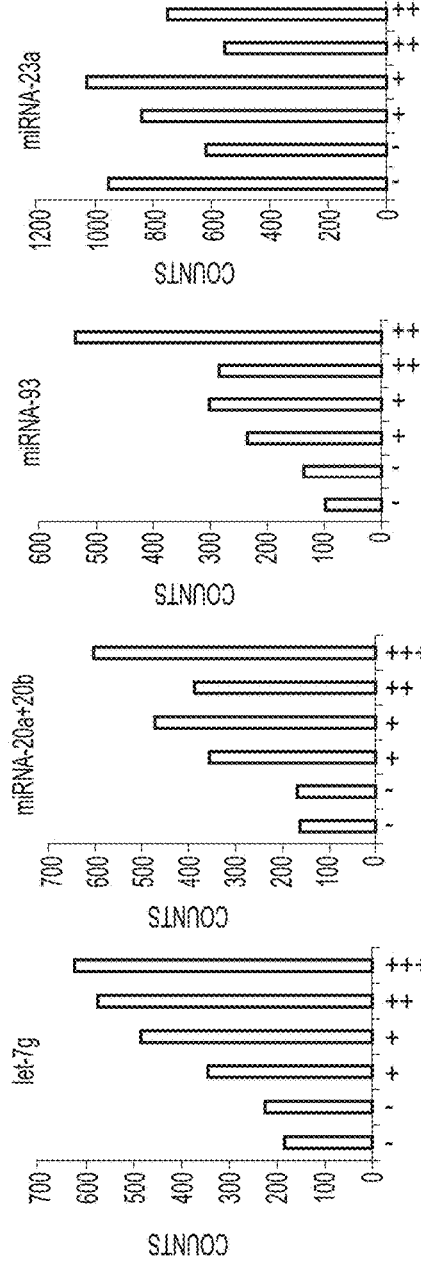

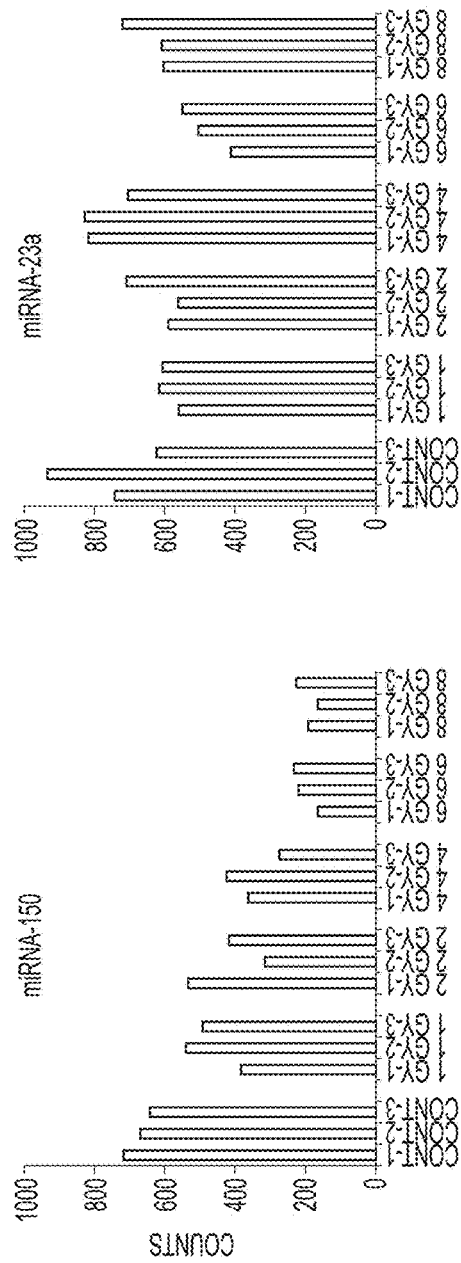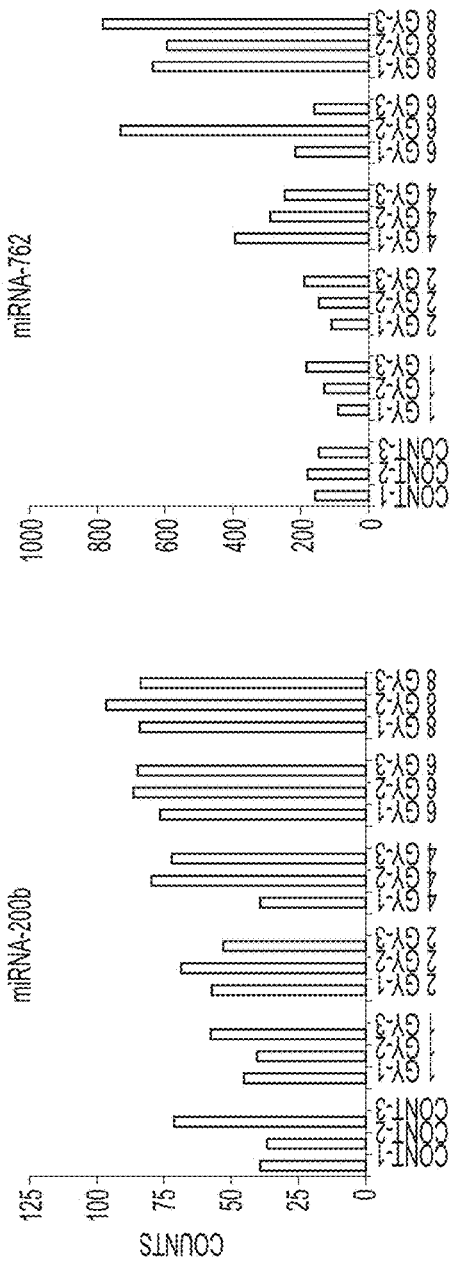

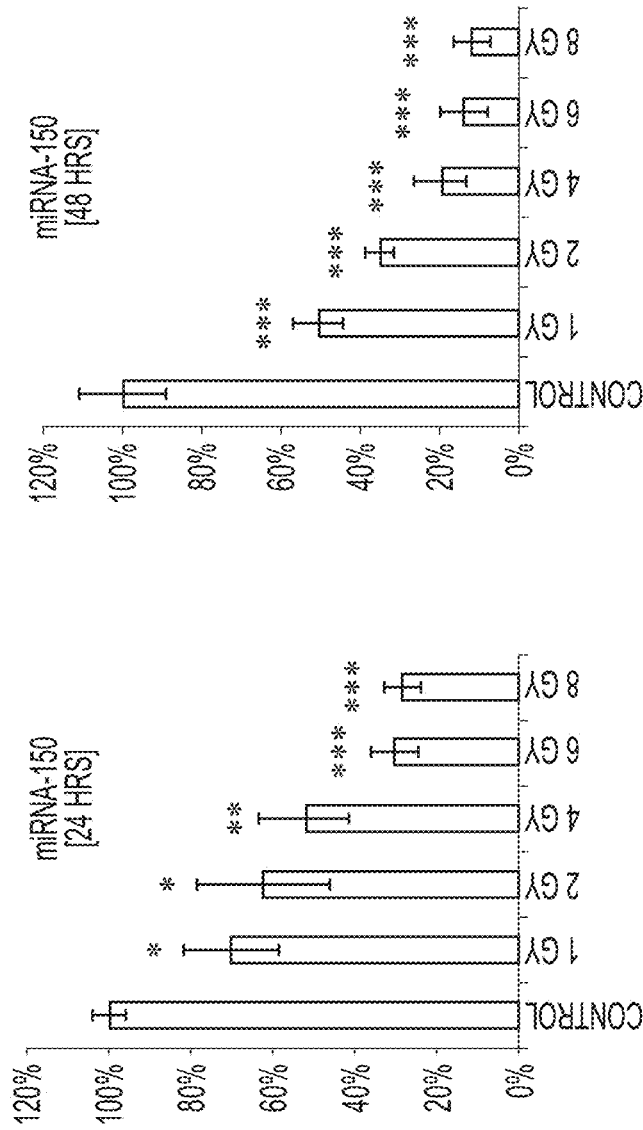
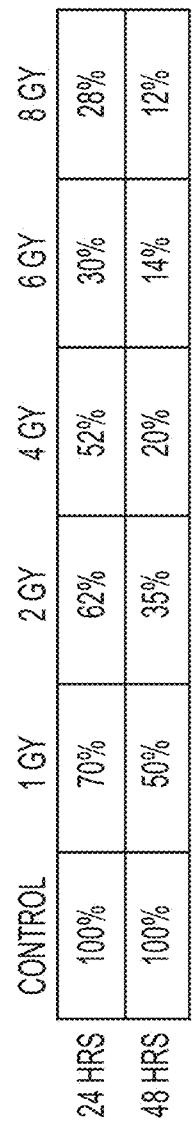
FIG. 6A  FIG. 6B  FIG. 6C

FRACTIONATION SCHEDULE

24H: 2 x 2 = 4 GY; SERUM: DAY 2
48H: 4 x 2 = 8 GY; SERUM: DAY 3
72H: 6 x 2 = 12 GY; SERUM: DAY 4

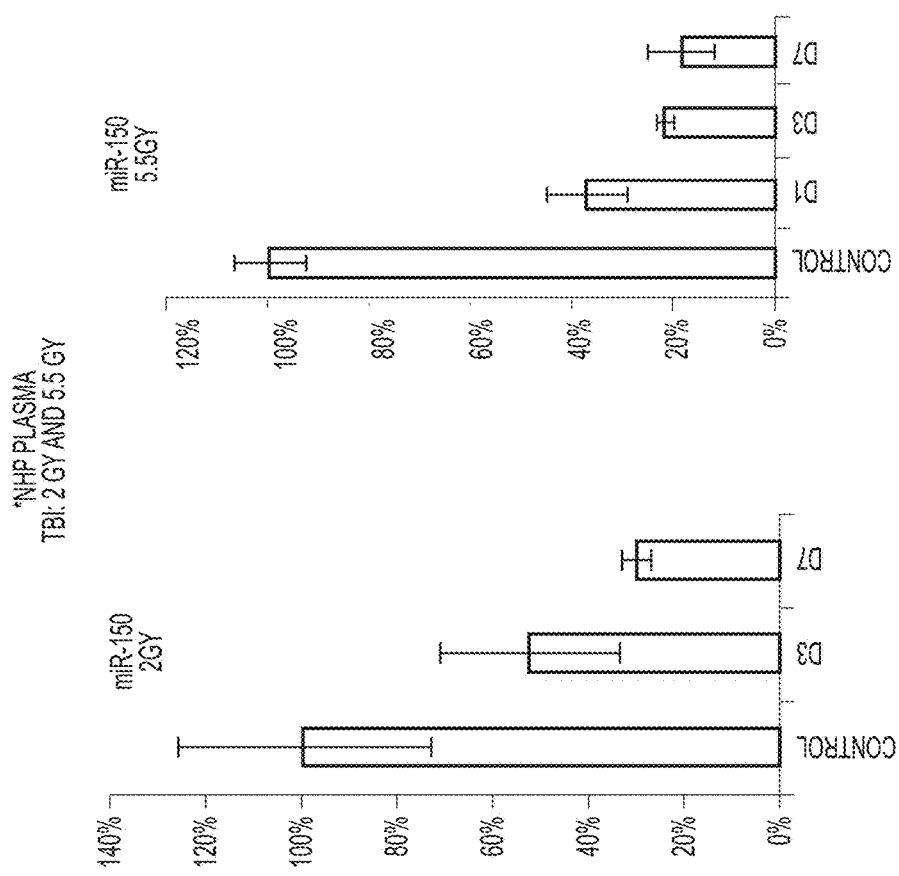

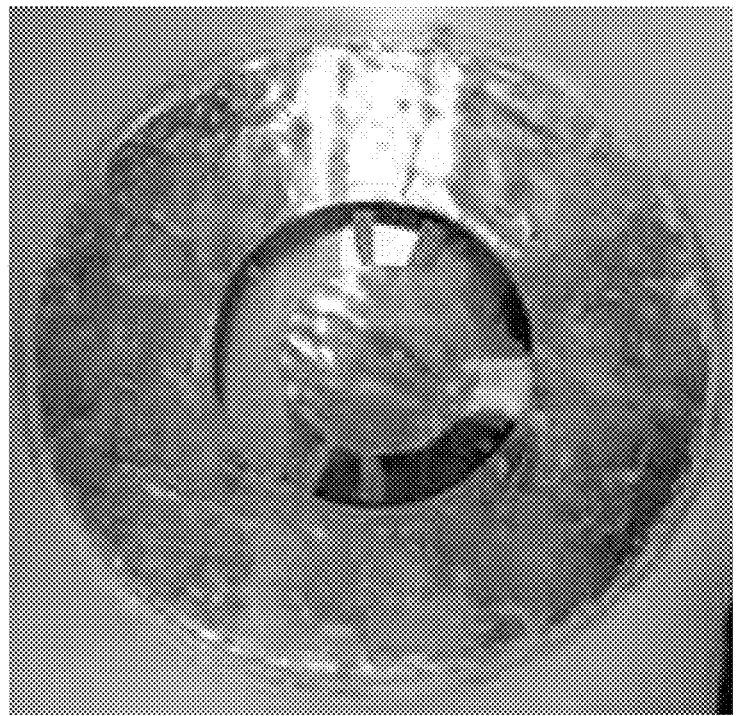
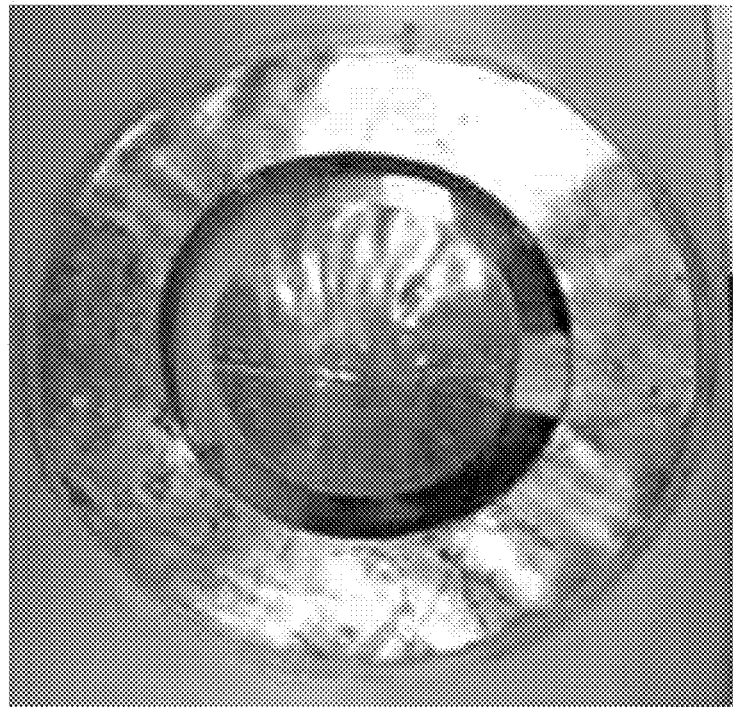
FIG. 10A

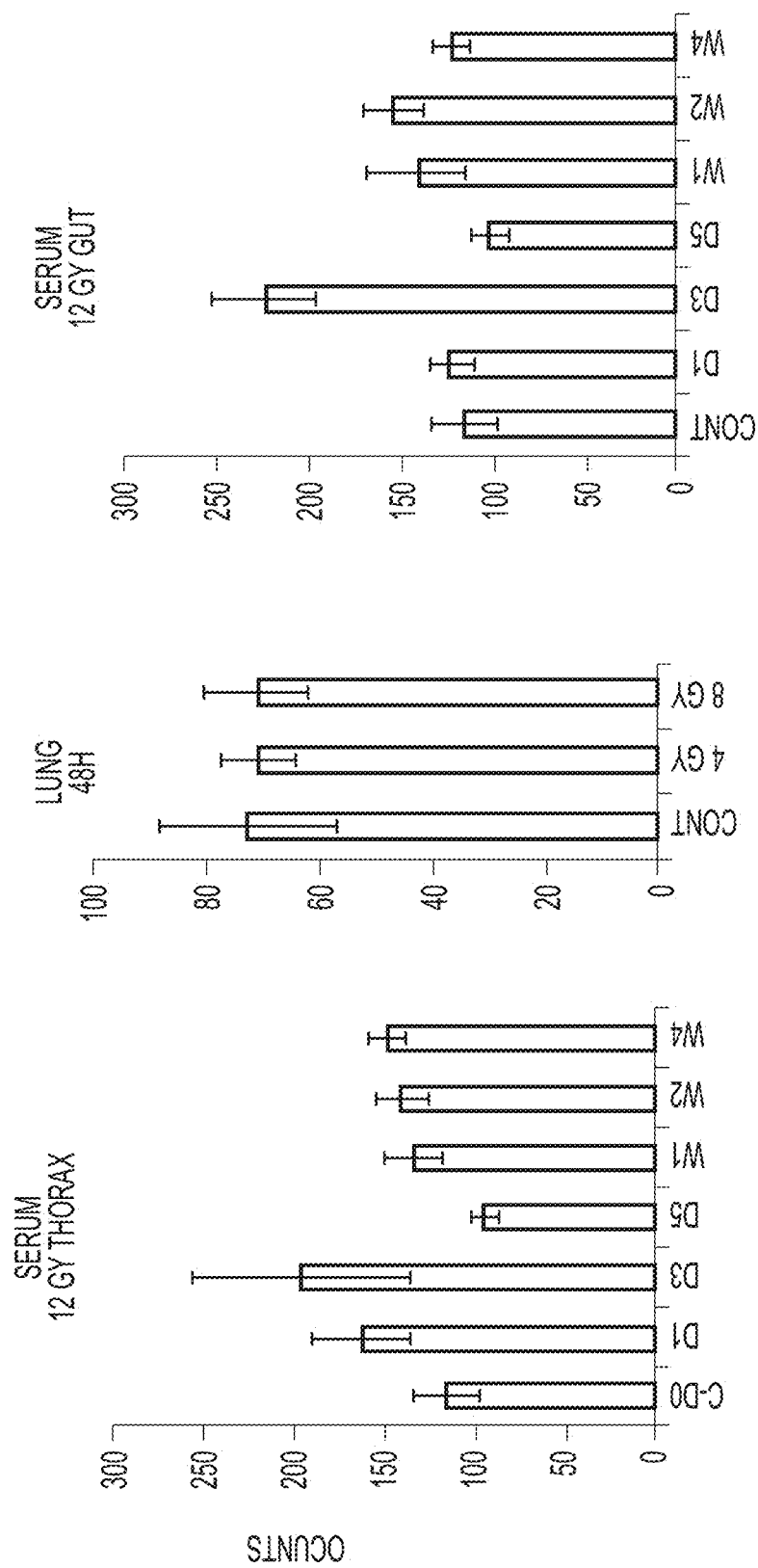

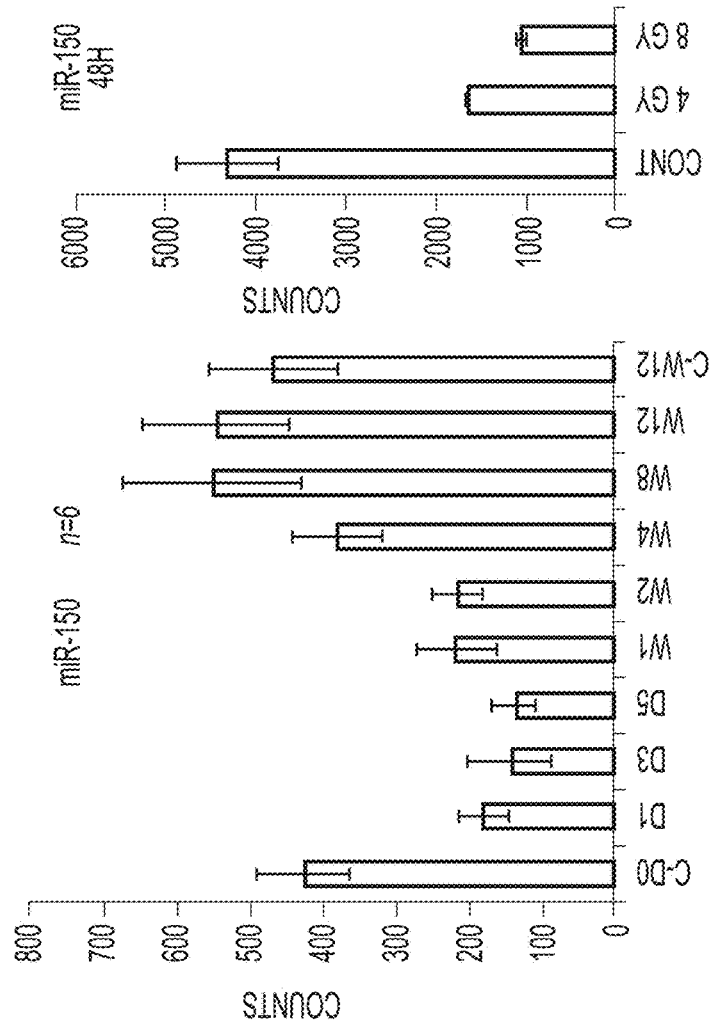

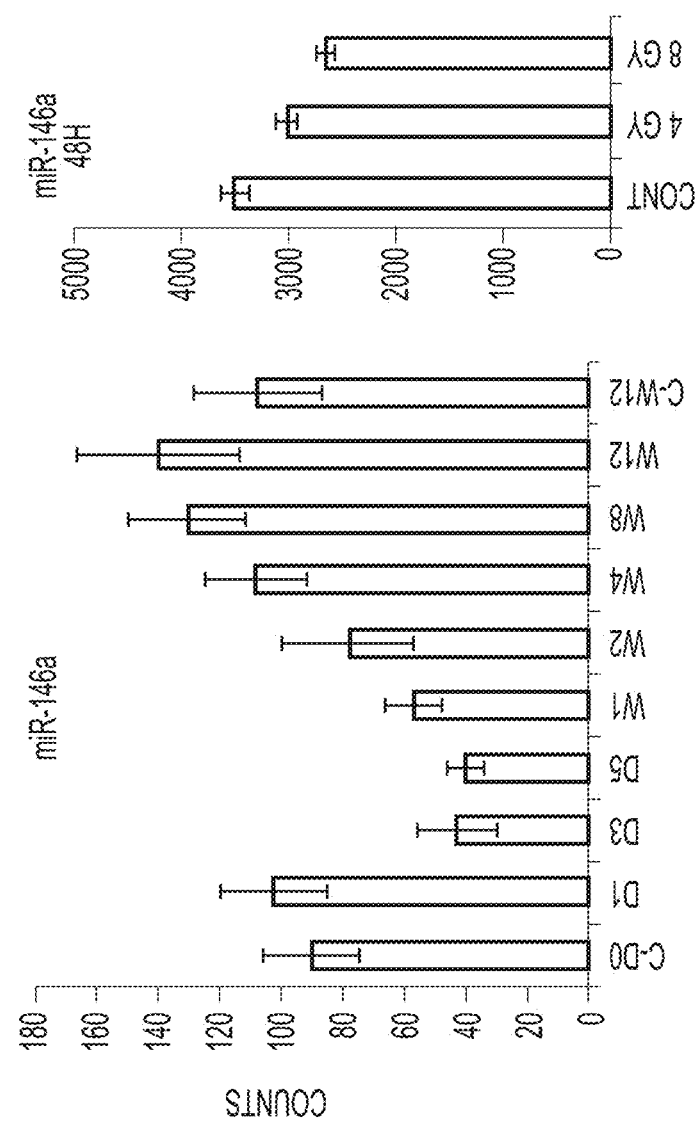

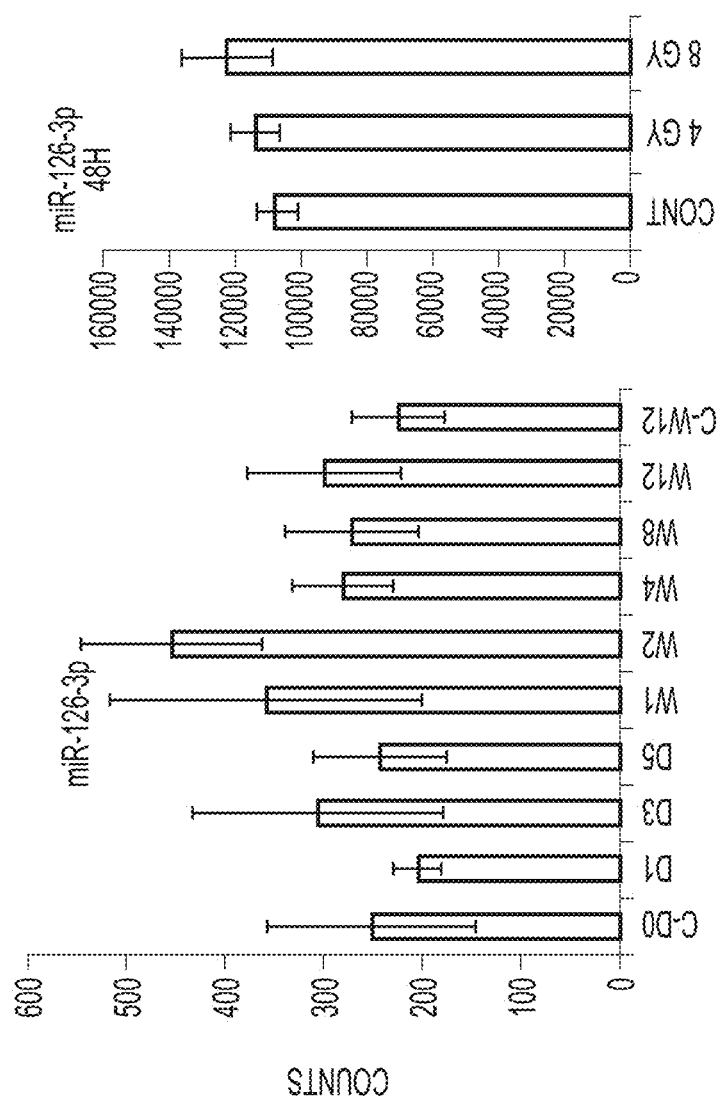

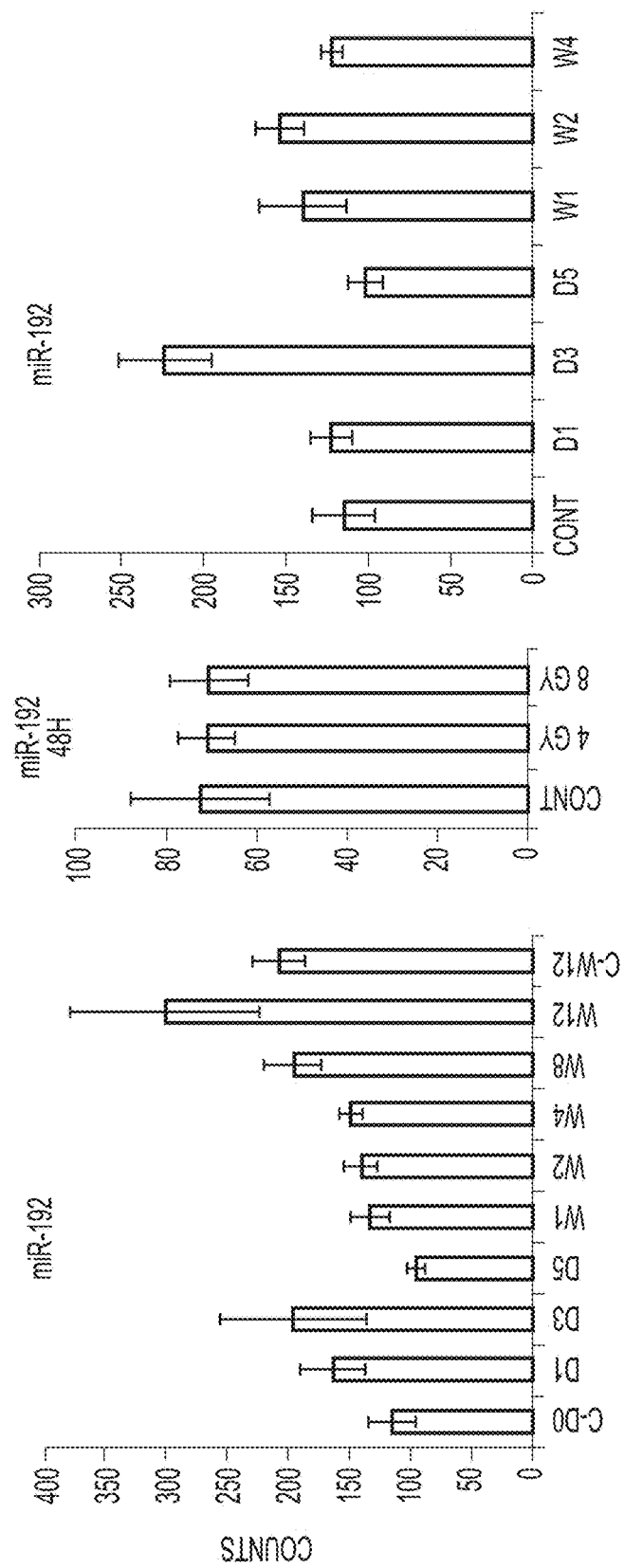

MIRNA BIOMARKERS FOR RADIATION BIODOSIMETRY

CROSS-REFERENCE TO RELATED APPLICATIONS

This application claims benefit of U.S. patent application Ser. No. 14/120,289, filed May 14, 2014, which claims benefit of U.S. Provisional Application No. 61/823,063, filed May 14, 2013, both of which are hereby incorporated herein by reference in their entirety.

STATEMENT REGARDING FEDERALLY SPONSORED RESEARCH OR DEVELOPMENT

This invention was made with Government Support under Grant No. U19AI067798-09 awarded by the National Institutes of Health. The Government has certain rights in the invention.

BACKGROUND

Management of radiological causalities that could occur from natural calamities, failures in operational safety mechanisms of nuclear power plants, or even a terrorist attack require immediate intervention from emergency responders and medical personnel. The damage caused by a meltdown can be catastrophic as it could release large amounts of radiation that quickly affects the environment and the health of surrounding population. Recent events involving the Fukushima Daiichi nuclear reactor have shown the unfortunate and immediate dangers posed by accidental radiation exposure. Nuclear exposure management protocols include rapid dose assessment for the affected population and identification of the individuals who require immediate medical attention. Development of robust biomarkers based on an individual's biological response is crucial for accurate assessment of the level of exposure and making important medical decisions. A personalized assessment will allow evaluation of an individual's physiological response to radiation damage. The calculated $LD_{50}$ for humans exposed to total body irradiation is in the range of 4.0 to 4.5 Gy and the dose range at which supportive care will be effective is narrow. Therefore, development of biomarkers for fast and accurate dose assessment is critical. Moreover, an individual's response varies depending on many confounding factors, such as immune status, age and genetics. These factors will ultimately determine a person's apparent response to exposure, and in some cases victims may not immediately exhibit visible signs of radiation damage. Therefore, physical dosimetry alone, and the available protein markers such as cytokines, have limitations to accurately estimate the dose and response of an individual.

Acute effects (Acute Radiation Syndromes, ARS) manifest themselves as Hematopoietic, Gastrointestinal (GI), and Cerebrovascular syndromes. Studies have shown that individuals exposed to an intermediate dose (5-8 Gy) could die within a few weeks due to GI syndrome. Lower doses (2-5 Gy) that are not immediately lethal but compromise the hematopoietic system can increase susceptibility to infection and death within months if supportive care is not provided in time [Waselenko J K, et al. (2004) Ann Intern Med 140:1037-1051; MacNaughton W K (2000) Aliment Pharmacol Ther 14: 523-528; Hall E J, et al. (2012) Radiobiology for the Radiologist. Seventh Edition: 193-200; Singh V K, et al. (2009) Exp Hematol 38: 61-70; Hanson W R, et al. (1984) Radiat Res 100: 290-297; Shimizu Y, et al. (2010) BMJ 340: b5349]. In addition, several of the victims who show little or no signs of acute radiation sickness could find themselves dealing with late effects in the form of cancer, pulmonary fibrosis, and chronic or progressive heart and kidney diseases. Epidemiological studies on survivors of the Hiroshima and Nagasaki A-bombs and Chernobyl nuclear accident showed an increased incidence of various cancers and cardiovascular diseases [Shimizu Y, et al. (2010) BMJ 340: b5349; Preston D L, et al. (2003) Radiat Res 160: 381-407]. Thus, development of biomarkers capable of accurately estimating the dose absorbed is important for identifying the individuals at risk for acute as well as late effects. Understanding the dose exposed can help in the making of medical decisions and timely administration of immune-modulators and mitigators. Development of such biomarkers can also help understand the response and toxicity in patients receiving therapeutic radiation, particularly for those who receive total body irradiation as a preparative step for bone marrow transplantation.

Over the last several years, there have been attempts to estimate the radiation dose exposed using hematological, biochemical, and cytogenetic parameters [Blakely W F, et al. (2010) Health Phys 99 Suppl 5: S184-191; Ossetrova N I, et al. (2010) Health Phys 98:204-208; Blakely W F, et al. (2010) Health Phys 98: 153-159]. Several protein markers such as C-reactive protein, amylase, and cytokines, such as transforming growth factors, have been investigated for their potential as biodosimeters [Blakely W F, et al. (2010) Health Phys 98: 153-159]. These protein markers, however, have large inter-individual variations; the readouts are indirect and fluctuate as a result of common variables such as inflammation and infection [Blakely W F, et al. (2010) Health Phys 99 Suppl 5: S184-191; Blakely W F, et al. (2010) Health Phys 98: 153-159]. Currently, lymphocyte depletion kinetics, clinical observation, and the dicentric chromosome (DC) assay are used for post exposure dose assessment. Lymphocyte depletion analysis requires repeated measurements over a prolonged period of time and the DC assay is highly technically involved and labor intensive [Blakely W F, et al. (2010) Health Phys 99 Suppl 5: S184-191; Chng W J, et al. (2004) Clin Diagn Lab Immunol 11: 168-173]. Therefore, there are needs for identification of biomarkers that are sensitive to incremental changes in dose, are robust and stable for days after exposure, and repeatedly assayable in a non-invasive or minimally invasive manner.

SUMMARY

Disclosed herein are compositions and methods for measuring exposure of a mammalian subject to ionizing radiation. The methods generally involve determining in a cell-free biological sample (e.g., serum or plasma) from the subject the levels of at least one radiation-sensitive miRNA whose blood levels are radiation dose- and time-dependent. The method can further involve determining in the sample the levels of at least one internal control miRNA whose blood levels are not radiation dose- and time-dependent. These internal control miRNA levels can then be used to normalize the radiation-sensitive miRNA levels. In some embodiments, the normalized levels of radiation-sensitive miRNA in the sample are a measure of the ionizing radiation exposure by the mammalian subject.

Examples of radiation-sensitive miRNA disclosed herein include let-7c, miR-15b, miR-21, miR-25, miR-29a, miR- 126-3p, miR-142-3p, miR-144-3p, miR-146a, miR-150, miR-191-5p, miR-192, miR-200b, miR-486, miR-574-5p, and miR-762.

In some embodiments, the radiation-sensitive miRNA is organ-specific and therefore useful for effectively triaging a subject after radiation exposure to determine which organs have been affected. Radiation-sensitive miRNA are disclosed that are specific for hematological, pulmonary, or gastrointestinal effects from ionizing radiation exposure. For example, miR-150 levels are shown to be specific for hematological effects of radiation on stem cell depletion and recovery in the bone marrow. In addition, miR-574-5p levels are shown to be specific for gastrointestinal effects from ionizing radiation exposure. The miRNAs let-7c, miR-15b, miR-21, miR-25, miR-29a, miR-126-3p, miR-142-3p, miR-144-3p, miR-146a, miR-191-5p, miR-192, miR-200b, and miR-486 are shown to be specific for pulmonary effects. These miRNA can in some cases also indicate the progression of injury to the lungs, including tissue damage that occurs in the first few days after exposure (miR-200b, miR-191-5p, miR-144-3p, miR-142-3p, miR-192), inflammatory response and injury that occurs after a couple of weeks (miR-21, miR-29a, miR-126-3p, let-7c, miR-191-5p, miR-15b), and Pneumonitis that occurs about eight weeks after exposure (miR-146a, miR-486, miR-25, miR-192).

Examples of miRNAs whose levels are not sensitive to radiation exposure and therefore can be used as internal controls include miR-30a, miR-23a, miR130b, and miR-302d-3p.

In some embodiments, the disclosed radiation-sensitive miRNAs are present in blood cells. Therefore, contamination of miRNA from blood cells, e.g., by hemolysis, can mask miRNAs that are organ specific and the result of radiation exposure. Therefore, in some embodiments, the disclosed method can further involve determining in the sample the levels of at least one hemolysis control miRNA whose presence in the sample is an indication of hemolysis contamination. In these embodiments, hemolysis contamination can be an indication that the sample should be discarded. Examples of miRNAs whose levels are an indication of hemolysis contamination include miR-451, miR-16, miR-25, miR-106b, let-7g, and miR-93.

To control for variances in the starting material as well as the efficiency of RNA extraction steps used for miRNA measurements, known amounts of spike-in controls can be used to control for these variations. The disclosed method can therefore also involve spiking the sample with known amounts of at least one oligonucleotide, and determining in the sample levels of the at least one oligonucleotide to further normalize the radiation-sensitive miRNA levels. Examples of suitable oligonucleotides include synthetic microRNAs.

The disclosed methods can involve triaging a subject using the disclosed microRNA as a dosimeter of radiation exposure, and then selecting an appropriate therapy for the subject depending on the exposure. For example, in some cases, the method involves treating the mammalian subject for radiation poisoning if the normalized levels of radiation-sensitive miRNA in the sample indicate exposure by the subject to remediable doses of ionizing radiation. For example, the subject can be treated with hematopoietic stem cell transplant, blood transfusion, or administration of growth factors, such as GM-CSF (Neupogen), within few days of whole body exposure a significant dose (e.g., 2 Gy and above) or a partial body exposure to a significant dose (e.g., 4 Gy and above). Alternatively, the method can involve treating the mammalian subject with palliative measures if the normalized levels of radiation-sensitive miRNA in the sample indicate exposure by the subject to irremediable doses of ionizing radiation.

Also disclosed is a radiation dosimeter that contains a plurality of oligonucleotides configured to measure levels of the disclosed microRNA. For example, the dosimeter can contain oligonucleotides configured to measure levels of at least one radiation-sensitive miRNA selected from the group consisting of let-7c, miR-15b, miR-21, miR-25, miR-29a, miR-126-3p, miR-142-3p, miR-144-3p, miR-146a, miR-150, miR-191-5p, miR-192, miR-200b, miR-486, miR-574-5p, and miRNA-762. For example, the at least one radiation-sensitive miRNA can comprise miR-150 to detect hematological effects of the radiation exposure. The at least one radiation-sensitive miRNA can also comprise miR-574-5p to detect gastrointestinal effects of the radiation exposure. The at least one radiation-sensitive miRNA can also comprise and at least one miRNA selected from the group consisting of let-7c, miR-15b, miR-21, miR-25, miR-29a, miR-126-3p, miR-142-3p, miR-144-3p, miR-146a, miR-191-5p, miR-192, miR-200b, and miR-486 to detect pulmonary effects of the radiation exposure.

The dosimenter can also contain oligonucleotides configured to measure levels of at least one internal control miRNA selected from the group consisting of miR-30a, miR-23a, miR-130b and miR-302d. The dosimeter can also contain oligonucleotides configured to measure levels of at least one hemolysis control selected from the group consisting of miR-451, miR-16, miR-25, miR-106b, let-7g, and miR-93.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A and 2B are lists of miRNAs detected in 20 μl serum from mice strains CBA/J (FIG. 2A) and C57BL/6 (FIG. 2B), arranged in their order of abundance (%) based on average signal (counts) detected. FIG. 2C is a partial list of miRNAs detected in rhesus monkey serum.

FIGS. 3A to 3H are a series of bar graphs measuring levels (counts) of miRNA-451 (FIG. 3A), miRNA-16 (FIG. 3B), miRNA-25 (FIG. 3C), miRNA-106b (FIG. 3D), let-7g (FIG. 3E), miRNA-20a+20b (FIG. 3F), miRNA-93 (FIG. 3G), and miRNA-23a (FIG. 3H) derived from red blood cells as a function of increasing levels (+) of hemolysis.

FIGS. 5A to 5D are bar graphs showing analysis of fold variations of selected serum miRNA biomarkers with a clear dose response. Histograms show variations in the fluorescent counts detected in the nCounter® multiplex assay, plotted against treatment. The counts obtained after normalization using multiple spike-in oligos were plotted for individual animals. FIG. 5A shows the dose dependent depletion of serum miRNA-150 at 24 hrs (p-values: 1 Gy-0.0164, 2 Gy-0.0191, 4 Gy-0.0026, 6 Gy-0.0001, 8 Gy-0.0001). FIG. 5B shows counts from a non-responsive molecule miRNA-23a, comparable to that of miRNA-150 in control animals. FIGS. 5C and 5D show radiation induced increase in miRNA-200b and miRNA-762 (p-values, miRNA-200b:1 Gy-0.7172, 2 Gy-0.4193, 4 Gy-0.4231, 6 Gy-0.0421, 8 Gy-0.0296; miRNA-762:1 Gy-0.4061, 2 Gy-0.1675, 4 Gy-0.0324, 6 Gy-0.3139, 8 Gy-0.001).

FIGS. 6A and 6B show dose and time dependent depletion of miRNA-150 in animals exposed to 1, 2, 4, 6 and 8 Gy with reference to controls analyzed at 24 hrs (FIG. 6A) and 48 hrs (FIG. 6B). Statistical analysis was performed using an unpaired two-tailed students t-test (*)=$p<0.05$; ()=$p<0.005$; (*)=$p<0.0005$. FIG. 6C shows kinetics of depletion of miRNA-150 as a function of dose and time relative to respective controls.

FIG. 8A shows the dose dependent depletion of serum miRNA-150 at different time points during and after fractionation (p-values: 4 Gy-0.0003, 8 Gy-0.0001, 12 Gy-0.0001). FIG. 8B shows counts from a non-responsive molecule miRNA-23a (control). FIGS. 8C and 8D shows radiation induced increases in miRNA-200b (p-values 4 Gy-0.014, 8 Gy-0.0047, 12 Gy 0.0027) and miRNA-762.

FIGS. 9C and 9D show the dose/time response of miR-150 in mouse serum (FIG. 9C) and rhesus monkey plasma (FIG. 9D). (*NHP-Rhesus macaques: Sample courtesy: ChromoLogic LLC).

FIG. 10A shows a sample set up for gut/whole thorax exposure.

FIGS. 11A to 11E show kinetics of serum miR-192 (FIGS. 11A to 11C) and miR-21 (FIGS. 11D and 11E) after WTLI (12 Gy) and Gut IR (12 Gy). Multiplex nCounter® assay was used to compare miRNAs in serum separated from blood collected on Day 1, 3, 5, Week 1, 2, and 4 after irradiation (n=6). Samples from age matched unirradiated animals were used as control. Counts (expression level) of the miRNAs in lung tissue also are shown.

DETAILED DESCRIPTION

Figure 1A:
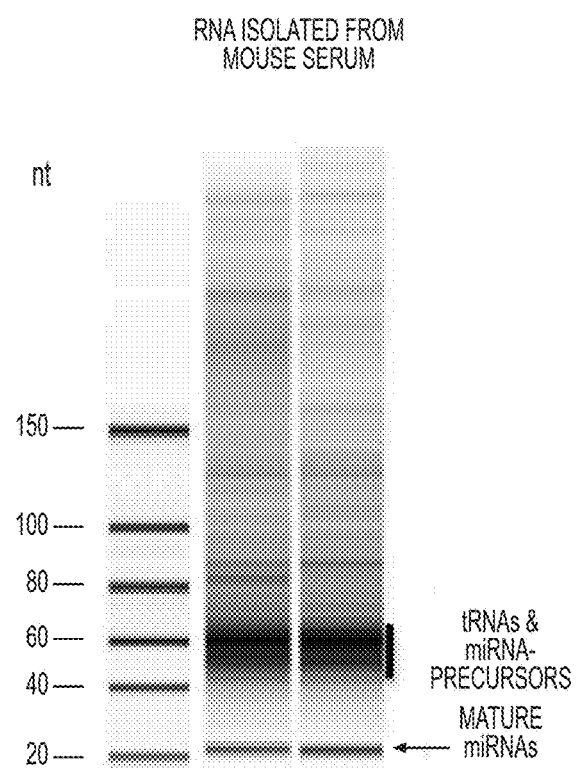
FIG. 1A is a gel image showing the integrity of RNA isolated from two mouse serum samples.

Disclosed are miRNA biomarkers which may be used to accurately measure radiation exposure levels by a subject. In addition, methods for triaging and treating radiation exposure, and radiation dosimeters are provided. In some embodiments, the methods entail detection of extracellular, circulating miRNAs in a suitable sample, preferably blood, plasma, serum, urine, or saliva.

In some embodiments, the biological sample used for determining the level of one or more miRNA biomarkers is a sample containing circulating miRNAs, e.g., extracellular miRNAs. Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA).

Extracellular miRNAs freely circulate in a wide range of bodily fluids. Accordingly, in some embodiments, the biological sample used for determining the level of one or more miRNA biomarkers is a bodily fluid, such as blood, fractions thereof, serum, plasma, urine, saliva, tears, sweat, semen, vaginal secretions, lymph, bronchial secretions, or CSF. In some embodiments, the sample is a sample that is obtained non-invasively. In some embodiments, the sample is obtained from a bodily fluid other than CSF. In some embodiments, the biological sample used for determining the level of one or more miRNA biomarkers may contain cells. In other embodiments, the biological sample may be free or substantially free of cells (e.g., a serum or plasma sample). The sample may likewise be free or substantially free of microvesicles. For example, a sample that is free or substantially free of microvesicles is one in which the microvesicle content of the sample is sufficiently low to avoid interfering with the ability to accurately determine the level of non-vesicular miRNAs in the sample.

The level of one or more miRNA biomarkers in a biological sample may be determined by any suitable method. Any reliable method for measuring the level or amount of miRNA in a sample may be used. Generally, miRNA can be detected and quantified from a sample (including fractions thereof), such as samples of isolated RNA by various methods known for mRNA detection, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString™ analysis, Northern Blot analysis, branched DNA (bDNA) signal amplification, and in situ hybridization), and sequencing-based methods (e.g. next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In other embodiments, the level of miRNA is measured during the amplification process. In still other embodiments, the level of miRNA is not amplified prior to measurement. Some exemplary methods suitable for determining the level of miRNA in a sample are described in greater detail below. These methods are provided by way of illustration only, and it will be apparent to a skilled person that other suitable methods may likewise be used.

Many amplification-based methods exist for detecting the level of miRNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of miRNA levels. Custom qRT-PCR assays to measure miRNAs in a biological sample, e.g., a body fluid, can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in biological samples.

Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the $2(-\Delta\Delta C(T))$ Method.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions. In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations.

miRNA may also be detected using hybridization-based methods, including but not limited to hybridization arrays (e.g., microarrays), NanoString™ analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

In one example of microarray detection, various oligonucleotides (e.g., 200+5'-amino-modified-C6 oligos) corresponding to human sense miRNA sequences are spotted on three-dimensional CodeLink slides (GE Health/Amersham Biosciences) at a final concentration of about 20 µM and processed according to manufacturer's recommendations. First strand cDNA synthesized from 20 µg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol.

Axon B-4000 scanner and Gene-Pix Pro 4.0 software or other suitable software can be used to scan images. Non-positive spots after background subtraction, and outliers detected by the ESD procedure, are removed. The resulting signal intensity values may be normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs in diseases. For example, RNA can be extracted from a sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner.

The fluorescence intensity of each spot is then evaluated in terms of the number of copies of a particular miRNA, using a number of positive and negative controls and array data normalization methods, which will result in assessment of the level of expression of a particular miRNA.

Total RNA containing the miRNA extracted from a body fluid sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA.

Several types of microarrays can be employed including, but not limited to, spotted oligonucleotide microarrays, pre-fabricated oligonucleotide microarrays or spotted long oligonucleotide arrays.

miRNAs can also be detected without amplification using the nCounter® Analysis System (NanoString™ Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter® miRNA assay kits are available from NanoString™ Technologies, which are capable of distinguishing between highly similar miRNAs with great specificity. miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.).

Northern Blot and in situ hybridization may also be used to detect miRNAs. Suitable methods for performing Northern Blot and in situ hybridization are known in the art.

Advanced sequencing methods can likewise be used as available. For example, miRNAs can be detected using Illumina® Next Generation Sequencing (e.g., Sequencing-By-Synthesis or TruSeq methods, using, for example, the HiSeq, HiScan, GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semiconductor sequencing.

Mass spectroscopy can also be used to quantify miRNA using RNase mapping. Isolated RNAs can be enzymatically digested with RNA endonucleases (RNases) having high specificity (e.g., RNase T1, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of posttranscriptional modifications can be revealed by mass shifts from those expected based upon the RNA sequence. Ions of anomalous mass/charge values can then be isolated for tandem MS sequencing to locate the sequence placement of the post-transcriptionally modified nucleoside.

Matrix-assisted laser desorption/ionization mass spectrometry (MALDI-MS) has also been used as an analytical approach for obtaining information about post-transcriptionally modified nucleosides. MALDI-based approaches can be differentiated from EST-based approaches by the separation step. In MALDI-MS, the mass spectrometer is used to separate the miRNA.

To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels.

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include standard (A, T or U, G and C) bases, or modified bases. Modified bases include, but are not limited to, the AEGIS bases (from Eragen Biosciences). In certain aspects, bases are joined by a natural phosphodiester bond or a different chemical linkage. Different chemical linkages include, but are not limited to, a peptide bond or a Locked Nucleic Acid (LNA) linkage.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay {e.g., TaqMan™) probes, stem-loop molecular beacons, stemless or linear beacons, peptide nucleic acid (PNA) Molecular Beacons, linear PNA beacons, non-FRET probes, Sunrise™/AmplifluorB™ probes, stem-loop and duplex Scorpion™ probes, bulge loop probes, pseudo knot probes, cyclicons, MGB Eclipse™ probe (Epoch Biosciences), hairpin probes, PNA light-up probes, anti-primer quench probes, self-assembled nanoparticle probes, and ferrocene-modified probes.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels. In some aspects, a label is attached to one or more probes and has one or more of the following properties: (i) provides a detectable signal; (ii) interacts with a second label to modify the detectable signal provided by the second label, e.g., FRET (Fluorescence Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g. biotin-avidin). In still other aspects, use of labels can be accomplished using any one of a large number of known techniques employing known labels, linkages, linking groups, reagents, reaction conditions, and analysis and purification methods.

miRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups.

In other embodiments, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

A probe ligation reaction may also be used to quantify miRNAs. In a Multiplex Ligation-dependent Probe Amplification (MLPA) technique, pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of miRNA biomarkers.

In some embodiments, where a subject is determined by the methods described herein to have been exposed to high doses of radiation, for example, enough to result in acute radiation syndrome (ARS), also disclosed are methods of treating such subjects for radiation poisoning.

ARS, also known as radiation poisoning, radiation sickness, or radiation toxicity, is a constellation of health effects which present within 24 hours of exposure to high amounts of ionizing radiation. The radiation causes cellular degradation due to damage to DNA and other key molecular structures within the cells in various tissues; this destruction, particularly as it affects ability of cells to divide normally, in turn causes the symptoms. The symptoms can begin within one or two hours and may last for several months. The terms refer to acute medical problems rather than ones that develop after a prolonged period. The onset and type of symptoms depends on the radiation exposure. Relatively smaller doses result in gastrointestinal effects such as nausea and vomiting and symptoms related to falling blood counts such as infection and bleeding. Relatively larger doses can result in neurological effects and rapid death.

Similar symptoms may appear months to years after exposure as chronic radiation syndrome when the dose rate is too low to cause the acute form or as delayed or late effects of the acute exposure. Radiation exposure can also increase the probability of developing some other diseases, mainly different types of cancers. These diseases are sometimes referred to as radiation sickness, but they are never included in the term acute radiation syndrome.

Classically acute radiation syndrome can affect the hematopoietic, gastrointestinal, pulmonary, and neurological/vascular systems. These symptoms may or may not be preceded by a prodrome. The speed of onset of symptoms is related to radiation exposure, with greater doses resulting in a shorter delay in symptom onset. These presentations presume whole-body exposure and many of them are markers which are not valid if the entire body has not been exposed. Each syndrome requires that the tissue showing the syndrome itself be exposed. The hematopoietic syndrome requires exposure of the areas of bone marrow actively forming blood elements (i.e., the pelvis and sternum in adults). The neurovascular symptoms require exposure of the brain. The gastrointestinal syndrome is not seen if the stomach and intestines are not exposed to radiation.

The hematopoietic syndrome is marked by a drop in the number of blood cells, called aplastic anemia. This may result in infections due to low white blood cells, bleeding due to low platelets, and anemia due to low red blood cells. These changes can be detected by blood tests after receiving a whole-body acute dose as low as 0.25 Gy, though they might never be felt by the patient if the dose is below 1 Gy. Conventional trauma and burns resulting from a bomb blast are complicated by the poor wound healing caused by hematopoietic syndrome, increasing mortality.

The gastrointestinal syndrome often follows absorbed doses of 6-30 Gy. Nausea, vomiting, loss of appetite, and abdominal pain are usually seen within two hours. Vomiting in this time-frame is a marker for whole body exposures that are in the fatal range above 4 Gy.

The neurovascular syndrome typically occurs at absorbed doses greater than 30 Gy, though it may occur at 10 Gy. It presents with neurological symptoms such as dizziness, headache, or decreased level of consciousness, occurring within minutes to a few hours, and with an absence of vomiting. It is invariably fatal.

Radiation induced lung injury can lead to pneumonitis (interstitial pulmonary inflammation) in 1-6 months. This often leads to fibrosis (scaring, collagen deposition) in 6 months to several years. Penumonitis and fibrosis causes respiratory distress and even death. Thoracic irradiation can also lease to lung cancer, breast cancer, lymphoma, etc.

The prodrome (early symptoms) of ARS typically includes nausea and vomiting, headaches, fatigue, fever, and short period of skin reddening. These symptoms may occur at radiation doses as low as 35 rads. These symptoms are common to many illnesses and may not, by themselves, indicate acute radiation sickness.

In the event of a large scale radiation accident or nuclear attack, a large number of individuals will need to be triaged to determine their dose of radiation exposure. The disclosed dosimeters and methods can be used to identify individuals who need treatment and those who do not. NIH guidelines indicate that individuals that receive 2 Gy and above need treatment. The DoD indicates that when combined with wound and burn, the critical dose for triage (to treat or not to treat) is 1.5 Gy.

Treatment is generally supportive with the use of antibiotics, blood products, colony stimulating factors, and stem cell transplant as clinically indicated. Symptomatic measures may also be employed. However, it is important to identify the organ(s) affected by the radiation and the dose they received in order to select the appropriate therapy for the subject.

For example, if it is determined that the hematopoietic system has been affected, then the subject can be treated with hematopoietic stem cell transplant, blood transfusion, or administration of growth factors, such as GM-CSF (Neupogen). In some cases, this treatment should occur within few days of whole body exposure of a significant dose (e.g., 2 Gy and above) or a partial body exposure to a significant dose (e.g., 4 Gy and above) with significant bone marrow coverage.

If it is determined that the GI track has been affected, the subject can be treated with intestinal stem cell therapy.

If it is determined that the lung has been affected, the subject can be treated with antioxidants and/or superoxide dismutase mimetics (e.g. AEOL 101050, a metalloporphyrin antioxidant developed by Aeolus). Corticosteroids (e.g. Dexamethasone) can be given to patients to subside penumonitis. The disclosed methods can identify individuals at risk of pneumonitis and thereby allow early administration of corticosteroids before the expression of the issue. Also the panel will help in testing the efficacy of mitigators.

The treatment of established or suspected infection following exposure to radiation (characterized by neutropenia and fever) is similar to the one used for other febrile neutropenic patients. However, important differences between the two conditions exist. Individuals that develop neutropenia after exposure to radiation are also susceptible to irradiation damage in other tissues, such as the gastrointestinal tract, lungs and central nervous system. These patients may require therapeutic interventions not needed in other types of neutropenic patients. The response of irradiated animals to antimicrobial therapy can be unpredictable, as was evident in experimental studies where metronidazole and pefloxacin therapies were detrimental. Antimicrobials that reduce the number of the strict anaerobic component of the gut flora (i.e., metronidazole) generally should not be given because they may enhance systemic infection by aerobic or facultative bacteria, thus facilitating mortality after irradiation.

An empirical regimen of antimicrobials can be chosen based on the pattern of bacterial susceptibility and nosocomial infections in the affected area and medical center and the degree of neutropenia. Broad-spectrum empirical therapy with high doses of one or more antibiotics can be initiated at the onset of fever. These antimicrobials can be directed at the eradication of Gram-negative aerobic bacilli that account for more than three quarters of the isolates causing sepsis. Because aerobic and facultative Gram-positive bacteria (mostly alpha-hemolytic streptococci) cause sepsis in about a quarter of the victims, coverage for these organisms may also be needed.

A standardized management plane of febrile, neutropenic patients must be devised in each institution or agency. Empirical regimens must contain antibiotics broadly active against Gram-negative aerobic bacteria (quinolones: i.e., ciprofloxacin, levofloxacin, a third- or fourth-generation cephalosporin with pseudomonal coverage: e.g., cefepime, ceftazidime, or an aminoglycoside: i.e. gentamicin, amikacin).

The anti-clotting compounds thrombomodulin (Solulin/Recomodulin) and activated protein C (Xigris) have also been shown to increase bone marrow cells needed for the production of white blood cells, and improve the survival rates of mice receiving lethal radiation doses by 40-80%.

Additionally, thrombopoietic activities of the glycosylflavanoids Orientin and Vicenin can be used to enhance the reconstitution of circulating platelets.

In some cases, hydration and palliative care is selected for subjects determined to have been exposed to lethal, irremediable doses of radiation.

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "radiation injury" refers to an injury or damage that is caused by exposure to ionizing radiation. Radiation injury includes but is not limited to radiation poisoning, radiation sickness, acute radiation syndrome or chronic radiation syndrome.

The term "ionizing radiation" refers to radiation that has sufficient energy to eject one or more orbital electrons from an atom or molecule (e.g. $\alpha$ particles, $\beta$ particles, $\gamma$ rays, x-rays, neutrons, protons and other particles having sufficient energy to produce ion pairs in matter).

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Identification of Sensitive Serum microRNA Biomarkers for Radiation Biodosimetry microRNAs (miRNAs) are non-coding RNAs of 19-22 nucleotides that were originally identified as regulators of gene expression by inducing cleavage of their target mRNA or blocking translation through base pairing to partially complementary sequences [Bartel D P (2004) Cell 116: 281-297]. miRNAs regulate diverse cellular processes including development, proliferation and differentiation, as well as various disease progressions [Iorio M V, et al. (2012) EMBO Mol Med 4:143-159]. In addition to their roles in post-transcriptional gene regulation, miRNAs in body fluids are proposed and have been assessed as biomarkers for various physiological responses and pathological stages [Cui W, et al. (2011) PLoS ONE 6: e22988; Scholl V, et al. (2012) Leuk Res 36:119-121; Qi P, et al. (2011) PLoS ONE 6: e28486; Weiland M, et al. (2012) RNA Biol 9: 850-859; Cortez M A, et al. (2011) Nat Rev Clin Oncol 8: 467-477;

Russo F, et al. (2012) PLoS ONE 7: e47786]. Earlier studies have detected miRNAs in a range of body fluids such as serum, plasma and urine, and miRNAs are relatively stable due to their smaller size and being protected in exosomes [Hunter M P, et al. (2008) PLoS ONE 3:e3694; Valadi H, et al. (2007) Nat Cell Biol 9: 654-659]. However, the current PCR based methods used for evaluation of miRNA in body fluids have limitations. Because several miRNAs are present in low quantities, PCR based detection and quantification often requires pre-amplification of the template and a higher number of amplification cycles, which compromises the reliability of the measurements [Etheridge A, et al. (2011) Mutat Res 717: 85-90]. To circumvent this problem, a digital amplification-free quantification and comparison method was used [Geiss G K, et al. (2008) Nat Biotechnol 26: 317-325] which allowed evaluation of the relative abundance of individual miRNAs in the serum samples and development of a panel of sensitive biomarkers for radiation biodosimetry.

Materials and Methods

Animal Studies

For animal studies involving acute single dose exposure, 8-9 week old *Mus musculus* were used. Male inbred mice (Strains CBA/J and C57BL/6, Jackson Laboratories) were co-housed (five per standard cage) and fed ad libitum. Mice were exposed to total body gamma radiation (TBI) using GammaCell@40 irradiator (Cesium 2137 Source) at a dose rate of 1.1 Gy/min. For each radiation dose (0, 1, 2, 4, 6 and 8 Gy) and time point (24 and 48 hrs) a minimum of five animals were used. Control animals were sham-exposed. For investigating the effect of fractionated dose, 15 animals were exposed to X-rays (in 2 Gy fractions) from a RS-2000 Biological Irradiator at a dose rate of 1 Gy/min. All the animal experiments were done with strict adherence to the institutional guidelines established and approved by the Ohio State University Animal Care and Use Committee (Permit number: 2011A00000029).

Blood was collected by submandibular bleeding or by cardiac puncture. Following coagulation (1 hr at room temperature), serum was separated using microtainer tubes (BD Biosciences) by centrifugation at 10,000 g for 10 min, and then frozen at −80° C. RNA was extracted using the Qiagen miRNA easy kit following the manufacturer's protocol. miRNAs were isolated from serum samples collected from 4-5 animals for each time points, and samples with high levels of hemolysis were excluded from analysis. In a typical isolation procedure, 100 ml serum was used. After lysis using QIAzol reagent, 4-20 pg synthetic oligonucleotides (spike-in oligos) Osa-miRNA-414, Cel-miRNA-248, At-miRNA-159a (Integrated DNA Technologies) were added prior to extraction. RNA was eluted in 100 ml water and concentrated to 20 ml and 3 ml was used for each assay for profiling using nanoString™ Technologies' multiplexed nCounter® platform. The platform incorporates fluorescent barcodes together with a digital readout for single-molecule imaging [Geiss G K, et al. (2008) Nat Biotechnol 26: 317-325]. It does not involve reverse transcription; instead the technology relies on sequence-specific probes to digitally measure miRNA abundance. This hybridization based amplification-free method allows processing of multiple samples, comparing and quantifying the number of molecules even of low abundance. The spike-in oligos allow a volume and quantity based normalization for detection of even small changes in individual miRNAs.

miRNA Expression Profiling

The digital multiplexed nanoString™ nCounter® mouse miRNA expression assay (nanoString™ Technologies) was performed with 10-30 ng total RNA isolated from a net volume of 20 ml serum as input material. Small RNA samples were prepared by ligating a specific DNA tag (miR-tag) onto the 39 end of each mature miRNA according to the manufacturer's instruction. These tags serve several purposes: they normalize the wide range of melting temperatures (Tms) of the miRNAs, provide a template to facilitate the use of the nanoString™ dual probe system, enable single base pair discrimination and specificity of highly homologous miRNA family members, and identify each miRNA species. Excess tags were removed by restriction digestion at 37° C. Hybridizations were carried out by combining 5 ml of each miRNA-miRTag sample with 20 ml of nCounter® Reporter probes in hybridization buffer and 5 ml of nCounter® Capture probes (for a total reaction volume of 30 ml) overnight at 65 uC for 16-20 hrs. Excess probes were removed using two-step magnetic bead based purification on the nCounter® Prep Station (NanoString Technologies). Abundances of specific target molecules were quantified on the nCounter® Digital Analyzer by counting the individual fluorescent barcodes and assessing the target molecules. For each assay, a high-density scan encompassing 600 fields of view was performed. The data was collected using the nCounter® Digital Analyzer after taking images of the immobilized fluorescent reporters in the sample cartridge with a CCD camera.

Data Analysis miRNA data analysis was performed using the nSolver™ software analysis, freely available from NanoString Technologies. The serum miRNA profiling data was normalized using the average signals obtained from three spike-in oligos, and miRNAs that gave significant hybridization signals were used for downstream analysis. ANOVA was performed with a cutoff p-value of 0.05 to identify a set of miRNAs that had the highest difference in means across samples. Coefficient of variance across samples was also performed with a cutoff of 0.4 and overlapping sets of miRNAs from the above two methods were selected as the most significant set. R software was used for the analysis.

Results

Optimization of Methods for Quantitative Analysis of Serum miRNAs

Figure 1B:
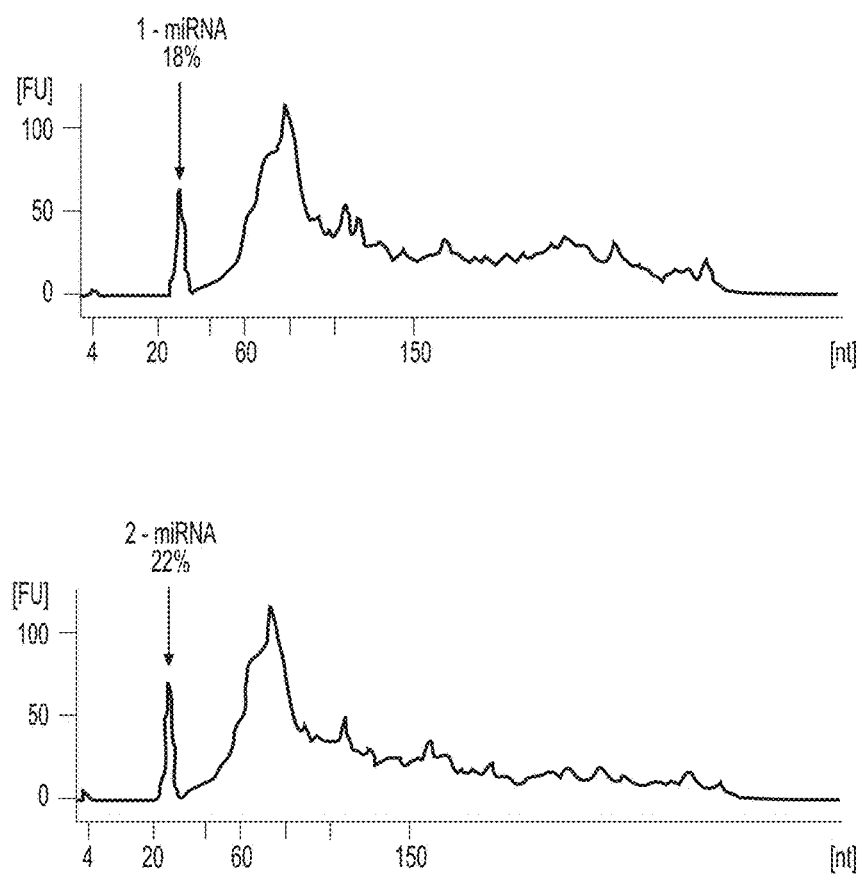
FIG. 1B shows densitometry traces used to quantify and compare the relative abundance of various small RNAs.

The digital multiplexed nanoString™ nCounter® mouse miRNA expression assay was performed on total RNA isolated from 20 ml of serum usually containing a total amount of 10-30 ng of RNA. The nCounter® multiplex platform is capable of detecting approximately 600 mouse specific miRNAs, four housekeeping genes and three non-mammalian miRNAs: Osa-miRNA-414, CelmiRNA-248 and At-miRNA-159a. During RNA isolation, synthetic oligonucleotides (spike-in oligos) corresponding to OsamiRNA-414, Cel-miRNA-248 and At-miRNA-159a were included as controls allowing the normalization of samples. The amounts of spike-in oligos were optimized by comparing their counts with that of endogenous miRNAs in serum samples. The optimal amount of spike-in oligos for normalization was identified to be 0.5-2 pg in each reaction. The inclusion of probes hybridizing to the house keeping genes enabled further identification and separate preparations with cellular RNA contaminations. The optimized method allowed detection of changes in serum miRNAs that are specific to changes in physiological and treatment conditions, such as response to radiation. The purity and integrity of the RNA recovered from serum samples was validated on a small RNA bioanalyzer (FIG. 1A). miRNAs were found to represent 18-22% of total serum RNA preparations (FIG. 1B).

The nCounter® expression profiling conducted on total RNA isolated from mice serum samples identified 88 miRNAs with high confidence. miRNA-451 was found to be the most abundant in serum preparations, contributing to 22-23% of total miRNAs (FIG. 2). miRNA-16 ranked second, representing, 13%. Analysis of serum samples from a minimum of three animals from each of the two strains of mice (CBA/J and C57BL/6) showed similar results. Several evolutionarily conserved and functionally significant miRNAs, such as miRNA-150, miRNA-21, miRNA-29a and miRNA-23a, were also detected in serum samples [Wang B, et al. (2012) Hepatology 56: 186-197; Thum T, et al. (2008) Nature 456: 980-984; Teichler S, et al. (2011) Blood 118: 1899-1902; Vasilescu C, et al. (2009) PLoS ONE 4: e7405; Zhou B, et al. (2007) Proc Natl Acad Sci USA 104: 7080-7085]. Given the abundance of miRNA-451 and miRNA-16 in serum, feasibility of using these as endogenous normalizers was investigated the by comparing their signals with that of spike-in oligos. However, because of the abundance of these miRNAs in red blood cells, even a small level of hemolysis was found to skew the results. Therefore, these endogenous markers were not used as biological normalizers. Furthermore, comparison of samples with increasing levels of hemolysis enabled identification of additional markers that potentially originating from the lysis of red blood cells. These include miRNA-25, miRNA-106b, let-7g, and miRNA-93 (FIG. 3), while the level of miRNA-23a was not increased in samples with higher levels of hemolysis. Thus, parallel analysis of samples normalized with multiple controls allowed identification of markers that are specific and sensitive to radiation treatment.

Radiation Dose Dependant Changes in Serum miRNA Profile Following Single Acute Dose Using the nCounter® multiplex assay, miRNAs in serum samples from control and irradiated animals collected 24 hrs after 1, 2, 4, 6 and 8 Gy total body irradiation (TBI) were compared. In order to minimize experimental error, irradiation, serum collection, RNA isolation, miRNA profiling, and normalization were done in parallel with controls and treatment groups. Samples with traces of cellular RNA contamination (with counts of 30 or above for any of the four housekeeping genes) were excluded from the analysis. Samples with high levels of hemolysis observed visually or based on relative abundance of miRNA-451 (23%), miRNA-16 (13%) correlating with increase in miRNA-25, miRNA-106b, let-7 g and miRNA-93 were also excluded from analysis.

Figure 4A:
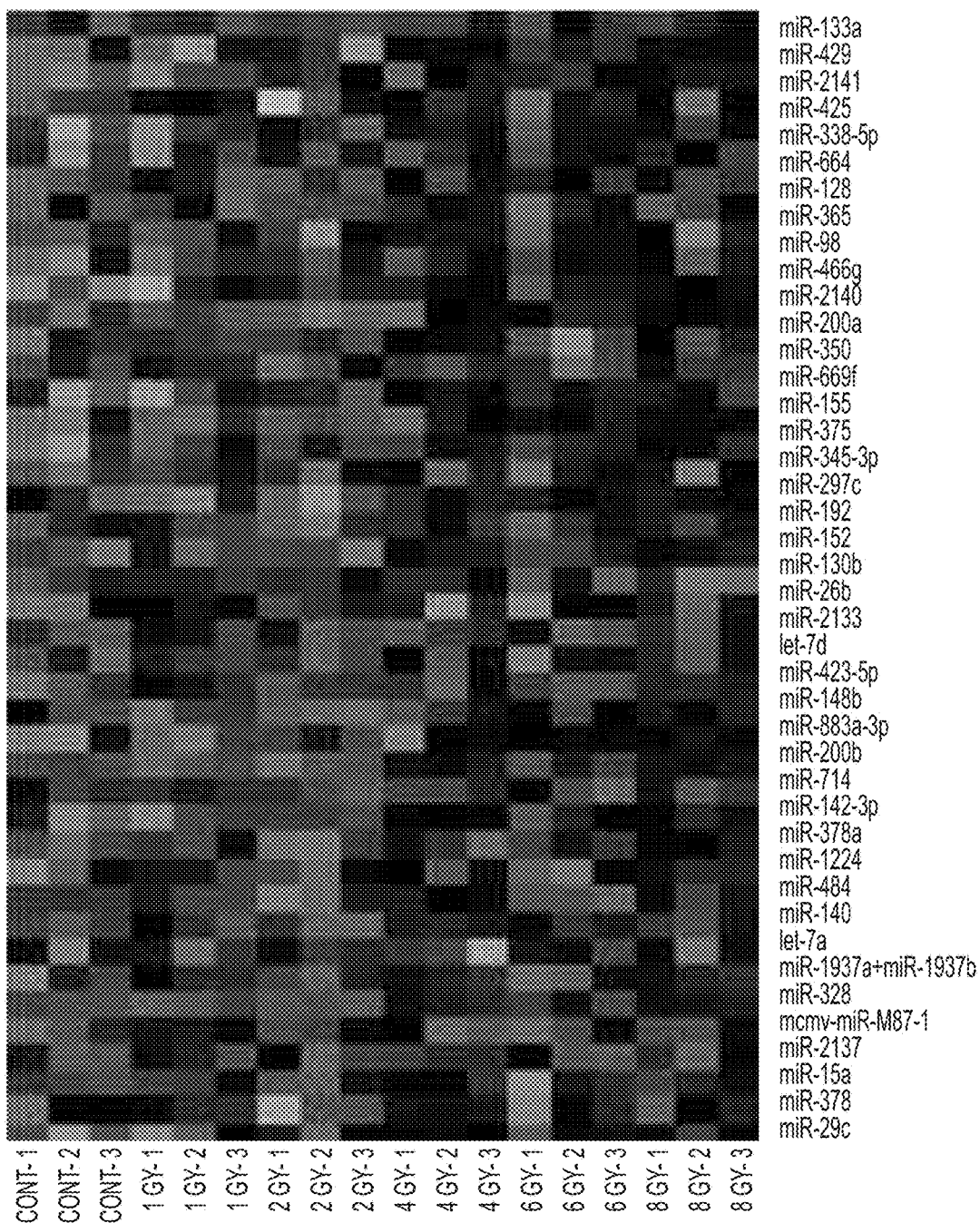
FIG. 4A is a heat map generated from the actual counts for 88 miRNAs detected in serum.
Figure 4A:
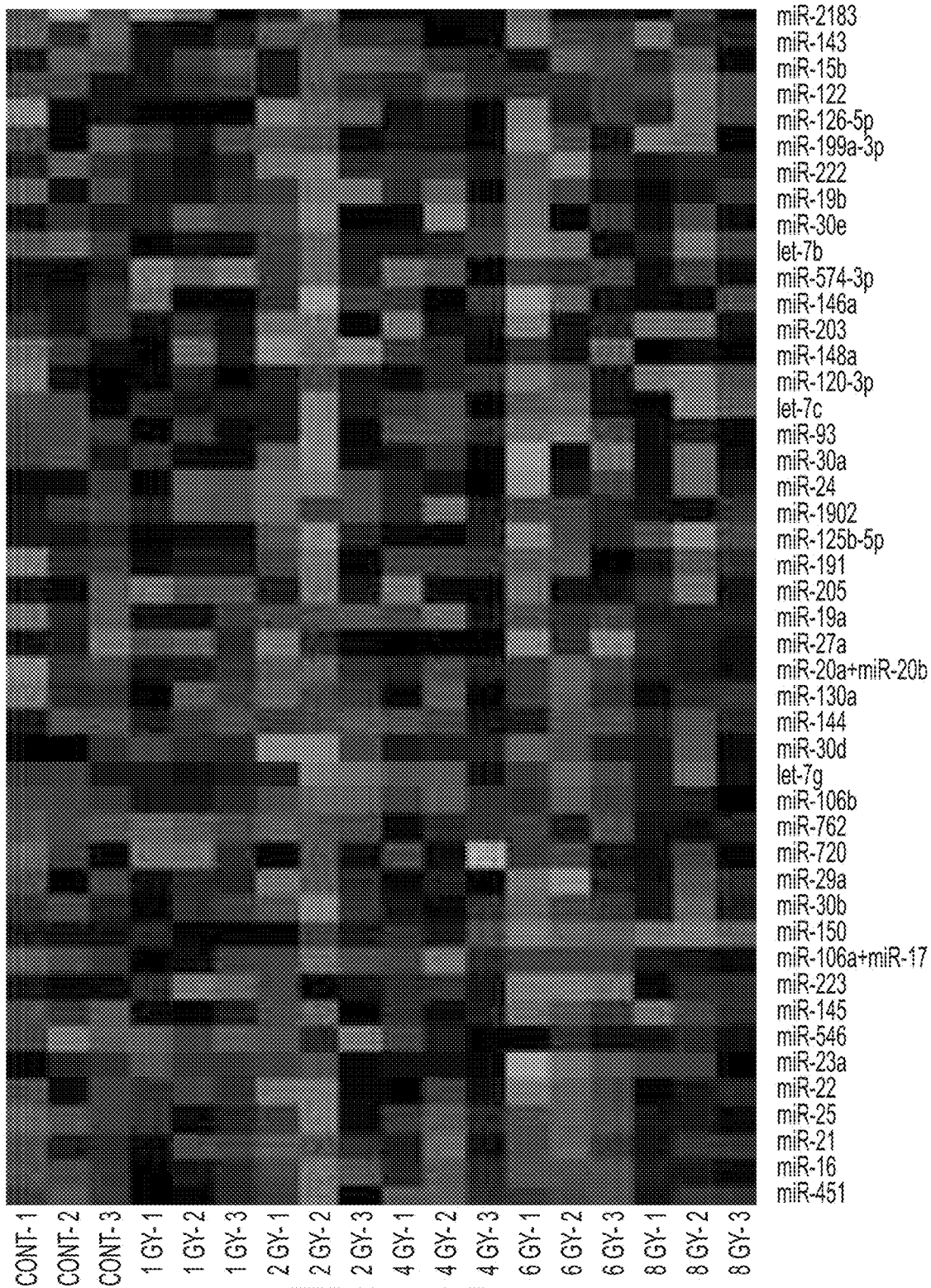
Figures 4B, 4C:
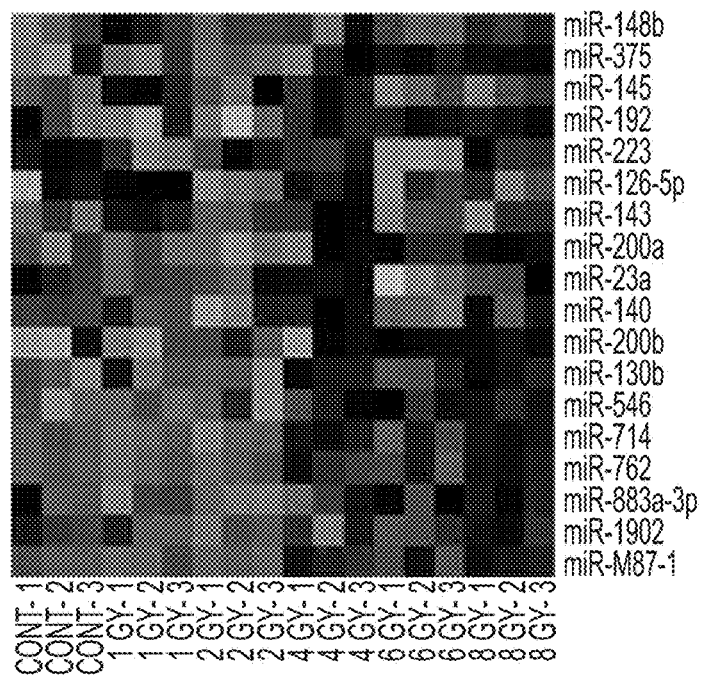
FIG. 4B is a heat map showing variations in a panel of 18 radio-responsive miRNAs, identified by ANOVA with a cutoff p-value of 0.05.
FIG. 4C is a dendrogram with a panel of markers identified with coefficient of variance across samples with a cutoff value of 0.4.
Figure 4D:
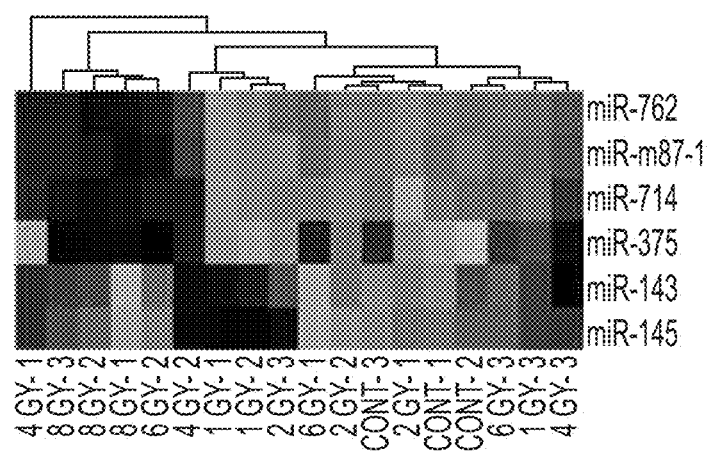
FIG. 4D is a heat map showing an overlapping set of miRNAs from ANOVA and CV.

The relative changes of 88 miRNAs detected in serum samples were evaluated for their radiation dose dependent changes (FIG. 4A). Changes were observed in several miRNAs distinguishable from irradiated versus controls and between different doses of radiation (FIG. 4B). At first, ANOVA was performed with a cutoff p-value of 0.05 to identify a set of miRNAs that had the highest difference in means across samples. Next, the coefficient of variance was calculated with a cutoff of 0.4 (FIG. 4C). Finally, an overlapping set of miRNAs from the above two methods was selected as the most significant and responsive set (FIG. 4D). Several markers were found clustering with specific dose or dose range indicating a clear radiation biodosimetry potential.

Selected radiosensitive miRNAs identified from cluster analysis were further investigated for their dose and time dependent changes. In order to evaluate the robustness of the response of each individual marker, the normalized fluorescence counts from individual animals that received varying doses of radiation was plotted (FIG. 5). miRNA-150 was identified as a robust radio-responsive serum biomarker, with a clear dose response in all animals compared 24 hrs after radiation (FIG. 5A). A decrease in levels of miRNA-150 was evident even in animals that received 1 Gy radiation, which further decreased with increasing dose (2, 4, 6 and 8 Gy). Molecules that exhibited an increase in their serum levels after radiation exposure include miRNA-200b and miRNA-762, and these changes were more pronounced in animals that received higher doses (FIG. 5C, 5D). miRNA-23a, whose counts in controls are comparable to that of miRNA-150, was used as another control (FIG. 5B).

miRNA-150 was further investigated for its kinetics of depletion by comparing the dose response at 24 and 48 hrs. A 30% reduction in serum miRNA-150 was observed in animals 24 hrs after 1 Gy total body radiation exposure, which further decreased to 50% by 48 hrs (FIG. 6). A time and dose dependent decrease in serum miRNA-150 was evident with an increase in dose, where a gradual decrease in counts was observed with increasing dose. This further confirms the sensitivity and robustness of this serum marker as a candidate for radiation biodosimetry.

Dose and Time Dependant Changes in miRNAs after Fractionated Radiation Exposure

Figure 7A:
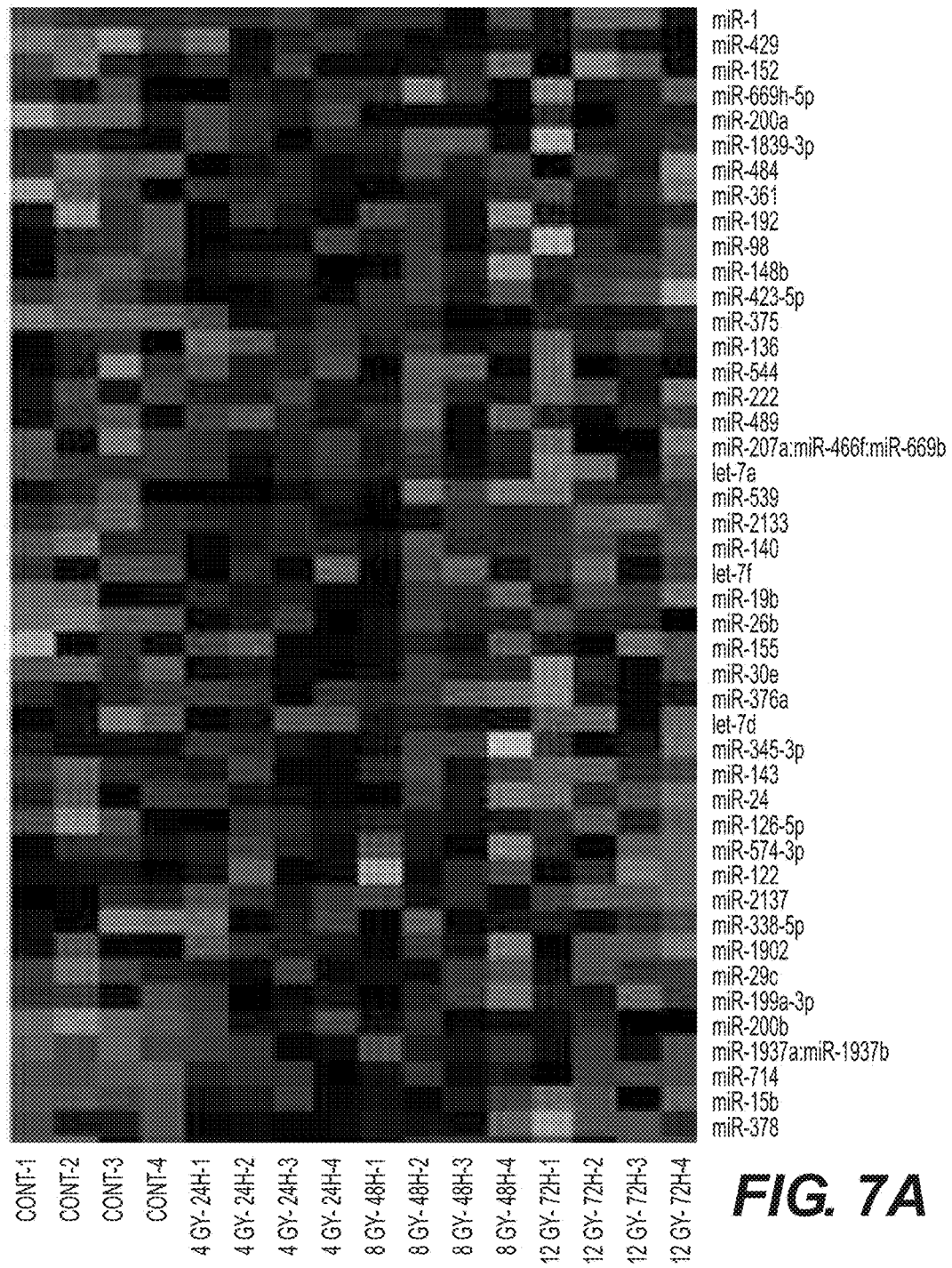
FIG. 7A is a heat map generated using the normalized data for 88 miRNAs detected in serum from four each of control and irradiated animals collected 24 hrs (2×2 Gy=4 Gy), 48 hrs (4×2=8 Gy) and 72 hrs (6×2 Gy=12 Gy).
Figure 7A:
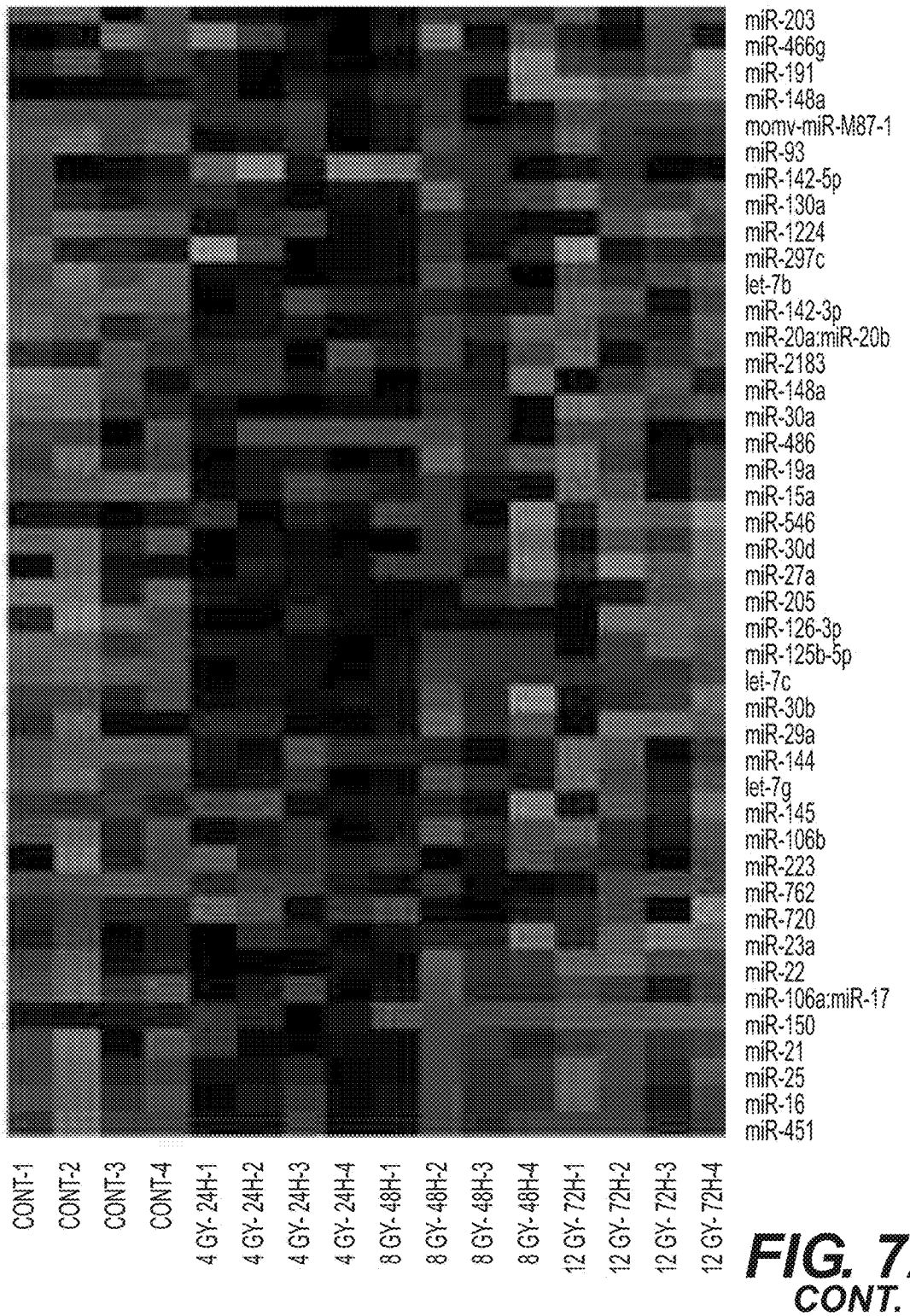
Figures 7B, 7C:
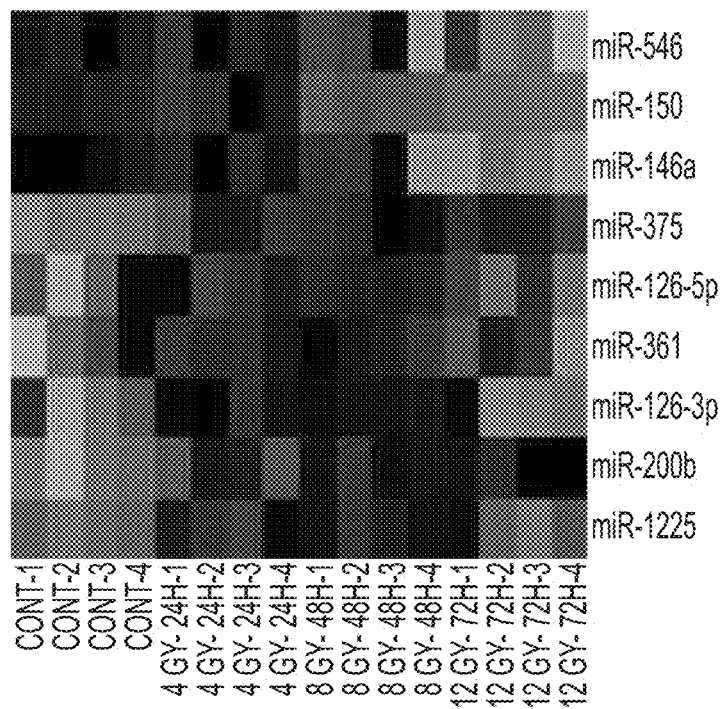
FIG. 7B is a scheme of the fractionation schedule.
FIG. 7C is a heat map for a panel of 8 miRNAs selected from ANOVA with a cutoff p-value of 0.05.
Figure 8A:
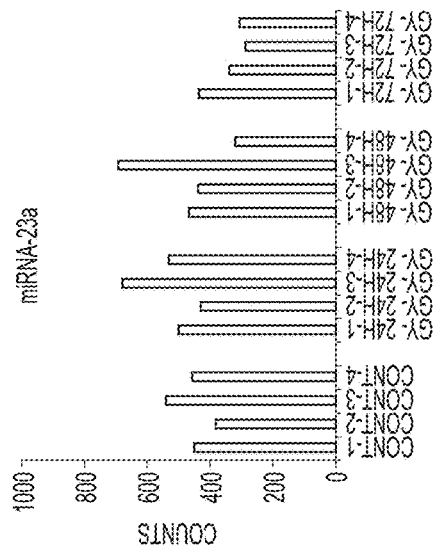
FIGS. 8A to 8D are bar graphs showing variations in the counts of miRNA-150 (FIG. 8A), miRNA-23a (FIG. 8B), miRNA-200b (FIG. 8C), and miRNA-762 (FIG. 8D) following fractionated radiation. The fluorescent counts obtained after normalization were plotted for individual animals with the dose and time as given.
Figure 8B:
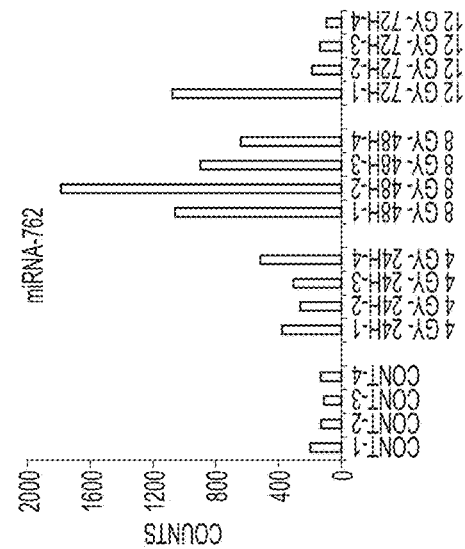
Figure 8C:
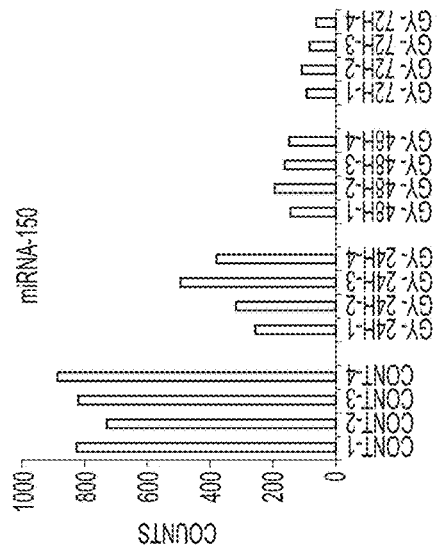
Figure 8D:
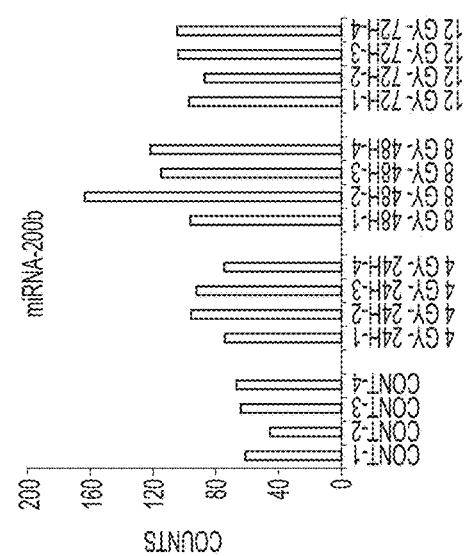

In order to further investigate the biodosimetry potential of the identified miRNAs in the setting of clinical therapeutic radiation, the changes in miRNAs in animals exposed to fractionated doses was compared. Mice were exposed to fractionated radiation following a schedule comparable to that administered to patients receiving total body irradiation as preparative regimen prior to bone marrow transplantation. Twelve week old mice were exposed to a total dose of 4, 8 and 12 Gy in 2 Gy fractions twice a day. Serum collected at 24 hrs (2×2 Gy=4 Gy), 48 hrs (4×2 Gy=8 Gy) and 72 hrs (6×2 Gy=12 Gy) was analyzed for changes in miRNAs using the multiplex nCounter® platform (FIG. 7). Serum collected from the same animals three weeks prior to radiation exposure was used to compare their basal levels, and the dose and time dependent changes. Moreover, several of those miRNAs that responded to acute single dose was found sensitive to fractionated radiation as well. Consistent with data from single acute dose, about 50% reduction in serum counts for miRNA-150 was observed in mice that received 4 Gy by 24 hrs. A further decrease was observed with higher doses at later time points (FIG. 8). Consistent with the response to single acute dose, markers such as miRNA-762 and miRNA-200b exhibited an increase in their serum levels under conditions of fractionated radiation up to 48 hrs. However, a decrease in miRNA-762 was observed at 72 hours. Overall, the data establishes the biodosimetry potential of selected miRNAs under conditions receiving acute single dose as well as fractionated radiation.

Discussion

The current study has identified several evolutionarily conserved miRNAs responsive to acute radiation in a dose range relevant to accidental radiation exposure or clinical radiation therapy. Identification of serum abundant radio-responsive and non-responsive miRNAs together with spike-in oligos provide a panel of markers and controls for developing radiation biodosimeters. This will aid rapid diagnostic screening to identify individuals who are at risk of developing acute radiation syndromes. Accurate dose evaluation is critical for making medical decisions and timely administration of mitigators to prevent or reduce the acute and late effects. Individual miRNAs such as miRNA-150 alone or in combination with other markers have the potential to estimate the dose to which the individual was exposed. The majority of serum miRNA markers did not respond to radiation, but the hierarchical clustering has identified several markers, potentially originating from blood cells, exhibiting dose- and time-sensitive responses to acute single or fractionated dose. In this study, 24 and 48 hr time points were used, which are realistic time frames to collect blood samples in a scenario involving mass causality from radiation exposure. miRNA-150 depletion kinetics indicate that the response is fast and robust with a near complete depletion in 48-72 hrs with 8 Gy acute dose and 8-12 Gy fractionated dose. The evaluation of the kinetics of depletion of miRNA-150 during three days of fractionation, using a schedule followed in a clinical setting, signifies the translational potential of this marker. In addition to chemo-based approaches, fractionated total body irradiation is used for conditioning in patients undergoing bone marrow transplantation. At the same time, management of hematopoietic injury is a major clinical question in both chemo and radiation based cancer therapies.

miRNA-150 is shown herein to be a sensitive biomarker for damage to the hematopoietic system, which is the most radiosensitive organ/system. The biodosimetry potential of miRNA-150 is evident from its time and dose dependent depletion, correlating with lymphocyte depletion kinetics [Waselenko J K, et al. (2004) Ann Intern Med 140:1037-1051; Blakely W F, et al. (2010) Health Phys 99 Suppl 5: S184-191; Goans R E, et al. (1997) Health Phys 72: 513-518]. Moreover, miRNA-150 is abundant in serum (ranked among the top 6 miRNAs in serum), and was found to be sensitive even at 1 Gy, the lowest tested dose in the current study. The time and dose response of this marker makes it a potential alternative to complete blood counts and lymphocyte depletion kinetics, the current diagnostic tools for evaluating radiation response.

Example 2: Organ Specific Biological Response to Radiation

Abstract

Figure 9A:
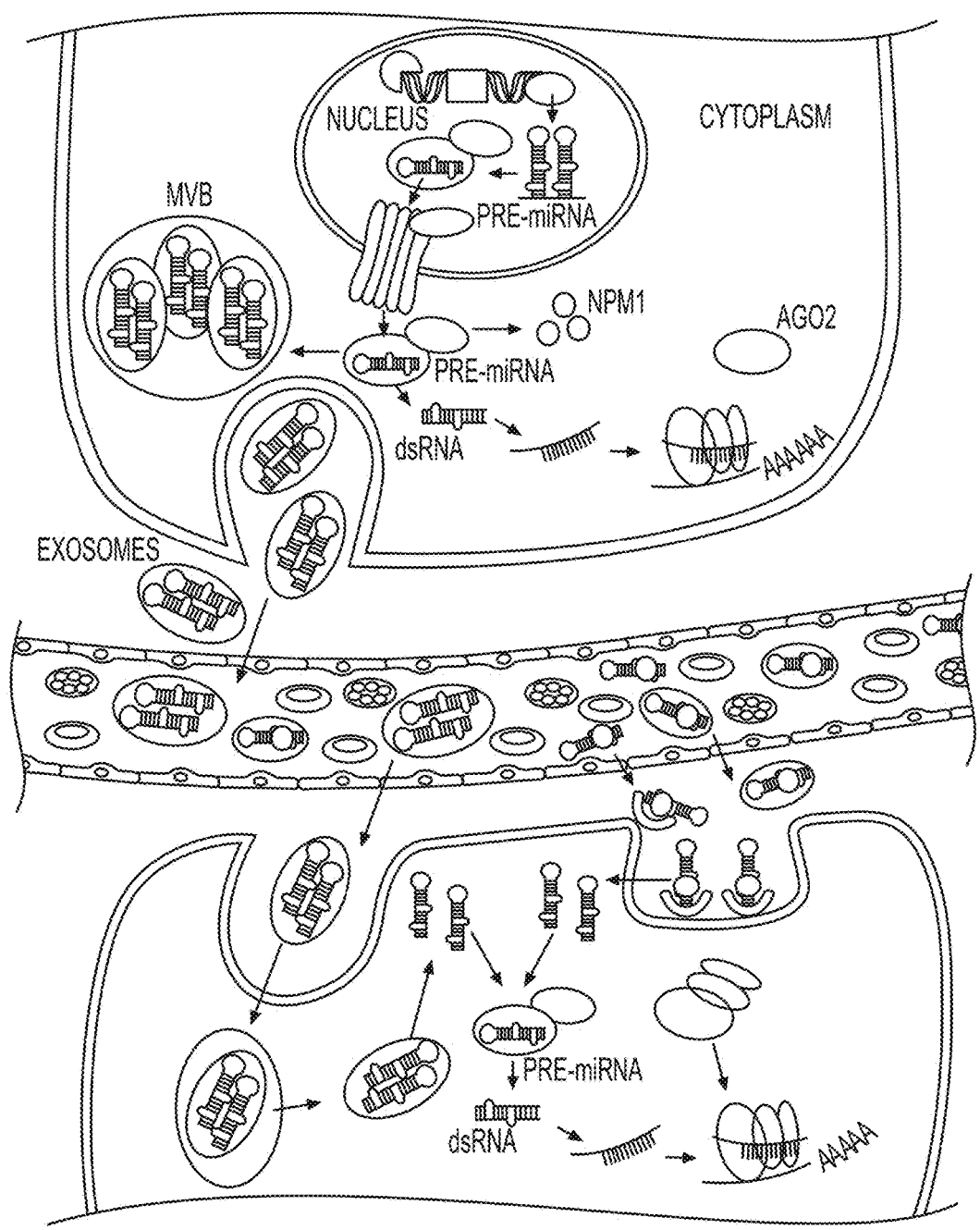
FIG. 9A illustrates the mechanism of release of miRNAs to blood stream.
Figure 9B:
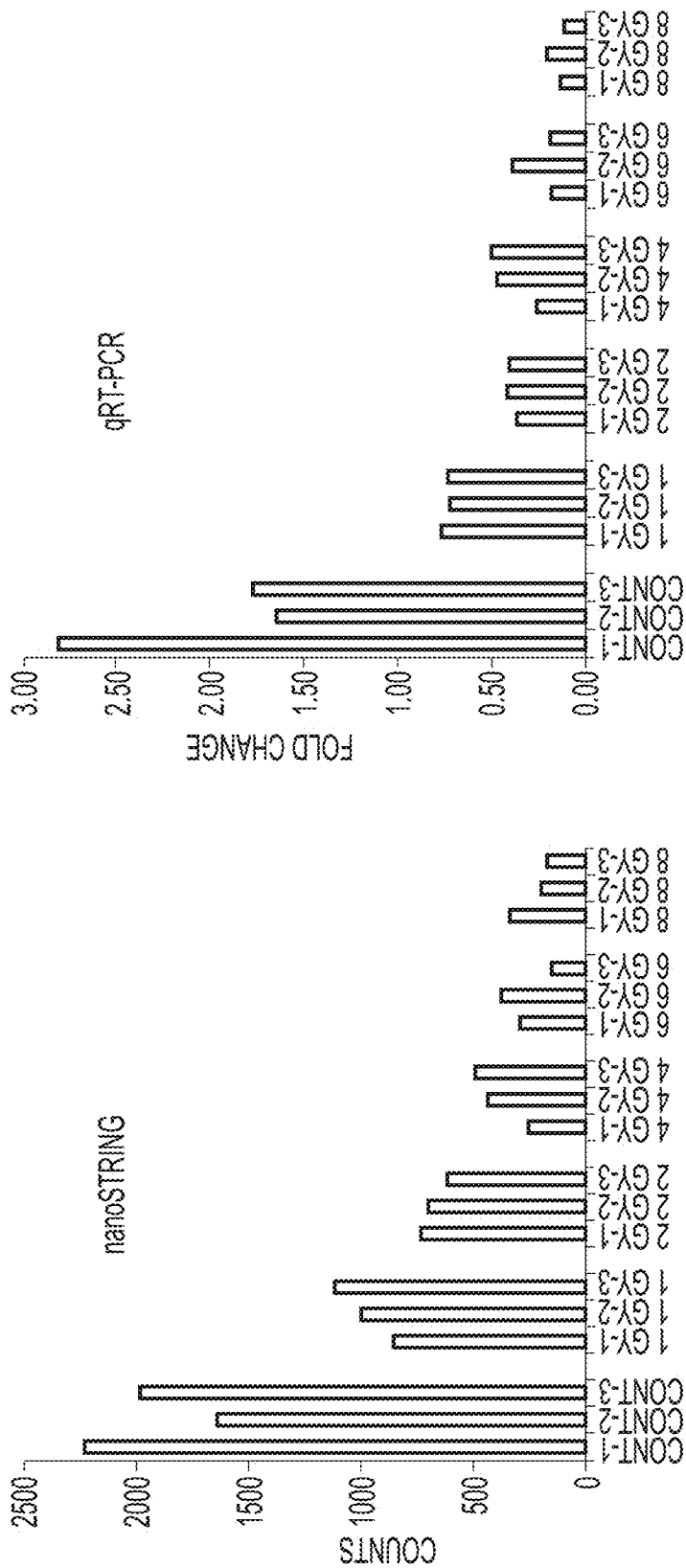
FIG. 9B shows miR-150 dose response after 48 hrs by nanoString™ and qRT-PCR, normalized with spike-in oligos.
Figure 9C:
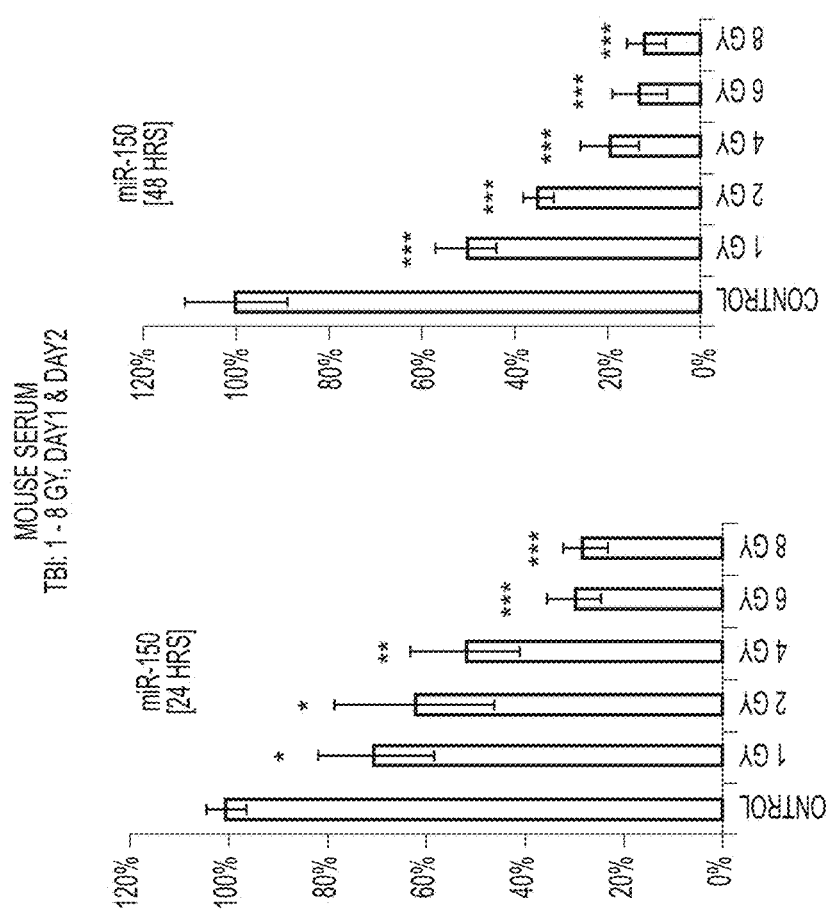
Figures 10B, 10C, 10D:
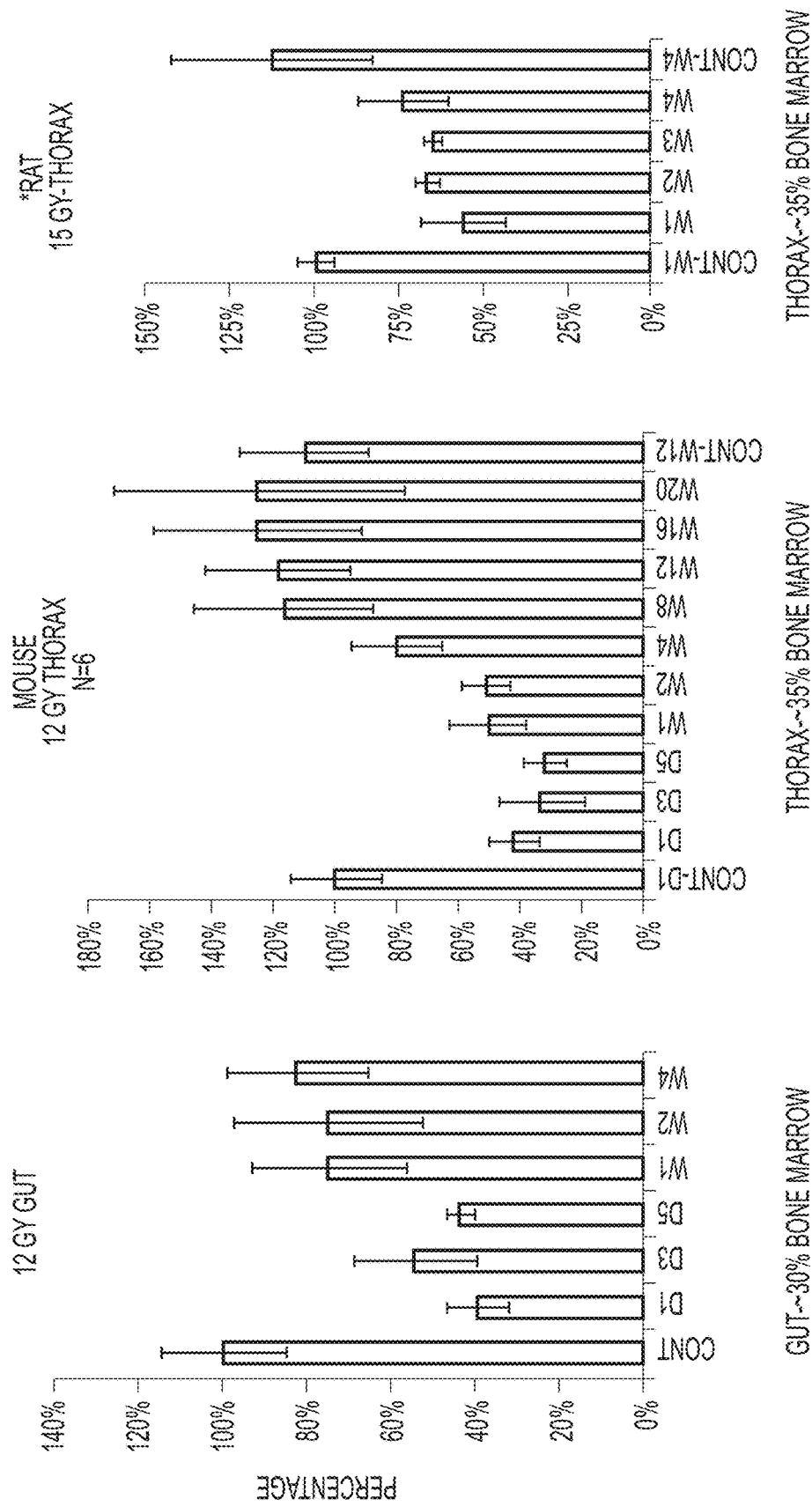
FIG. 10B shows the kinetics of miR-150 after gut irradiation (n=3)
FIGS. 10C and 10D show miR-150 kinetics after whole thorax lung irradiation (WTLI) in mouse (FIG. 10C, n=6) and in rats (FIG. 10D, n=4). Two sets of animals were used to bleed at early time points.

A major issue that affects the decision making in triage after radiation accidents is the heterogeneity due to variations in exposures [Prasanna, P. G., et al. (2010) Radiat Res 173(2):245-53; Rea, M. E., et al. (2010) Health Phys 98(2): 136-44]. In a partial body exposure event, depending on dose and geography of exposure, effect may be restricted to a single or multiple organs [DiCarlo, A. L., et al. (2011) Disaster Med Public Health Prep 5 Suppl 1:S32-44]. As such, ARS follows a deterministic effect whereby dose effects have distinct clinical outcomes: generally <2 Gy exhibit mild symptoms, 2-6 Gy are primarily hematologic (HE) effects, and above 5-6 Gy gastrointestinal (GI) effects are prominent which progress more rapidly [DiCarlo, A. L., et al. (2011) Disaster Med Public Health Prep 5 Suppl 1:S32-44; Waselenko, J. K., et al. (2004) Ann Intern Med 140(12):1037-51]. Damage to the GI system should be evident within days, however require a relatively higher dose than that needed to affect the HE system. Lung is a relatively sensitive organ; but the effects will not be apparent for weeks or even months [Garofalo, M., et al. (2014) Health Phys 106(1):56-72]. The current biodosimeters (lymphocyte depletion kinetics and dicentric chromosome assays) read the response in hematopoietic system. Because of the differences in the kinetics and latency period, it is difficult to detect and/or distinguish the effects on non-HE systems. In addition, the threshold and latency period could differ due to differences in age, immune status and other underlying conditions.

miRNAs as Radiation Response Markers miRNAs are small RNA molecules of 20-24 nt long originally identified as regulators of gene expression [Bartel, D. P., et al. (2004) Cell 116(2):281-97]. They are abundant in body fluids and hence provide useful tools for diagnosis by minimally-invasive assay. In body fluids including serum and plasma, miRNAs are protected in exosomes, microparticles, and nucleoprotein complexes. Thus, they are stable at room temperature for days and even after several freeze-thaw cycles [Mitchell, P. S., et al. (2008) Proc Natl Acad Sci USA 105(30):10513-8]. Being small, they are less susceptible to degradation. Levels of specific miRNAs in blood can change after radiation by multiple ways. Like in the case of mRNAs, expression level can be altered after radiation [Templin, T., et al. (2012) Int J Radiat Biol. 87(7):653-62]. They can be released with apoptotic bodies and/or by active secretary pathways. It has been shown that processing of the precursors of miRNAs can directly or indirectly be regulated by cytokines such as Tumor Necrosis Factor-α (TNFα) and TGFβ1[Barcellos-Hoff, M. H., et al. (1998) Radiat Res 150(5 Suppl):S109-20; Zhu, Y., et al. (2010) Int J Clin Exp Med 3(3):211-22; Davis, B. N., et al. (2008) Nature 454 (7200):56-61] that can be altered after radiation. Also, radiation induced activation of ATM kinase can cause alteration of the precursors in miRNAs [Zhang, X., et al., et al. (2011) Mol Cell 41(4):371-83]. Finally, reduction in a particular cell type (e.g. lymphocytes) will result in reduced circulating exosomes originated from that cell.

miR-150 as a Biodosimeter:

An amplification-free hybridization based nCounter® assay (>600 probes) was used to measure changes in over 80 miRNAs in serum after irradiation (gamma rays, 1.11 Gy/min, from Cs-137 source) [Jacob, N. K., et al. (2013) PLoS ONE 8(2):e57603]). A volume based normalization was used with a mixture of three spike-in oligos. Among various evolutionarily conserved miRNAs, miR-150 was identified as highly sensitive biomarker whose serum depletion correlates with radiation dose. miR-150 regulates B-cell development and is abundant in lymphocytes [Garzon, R., et al. (2008) Curr Opin Hematol 15(4):352-8; Adams, B. D., et al. (2012) Cell Rep 2(4):1048-60; Xiao, C., et al. (2007) Cell 131(1):146-59; Zhou, B., et al. (2007) Proc Natl Acad Sci USA 104(17):7080-5; Jiang, X., et al. (2012) Cancer Cell 22(4):524-35; Bezman, N. A., et al. (2011) J Exp Med 208(13):2717-31]. In mice that received acute single doses of 1, 2, 4, 6 and 8 Gy gamma-rays, a 30%, 38%, 48% 70% and 72% reduction of serum miR-150 was observed at 24 hrs, which was further reduced at later time points (FIG. 9B/9C). The results were confirmed by alternative methods such as qRT-PCR and RNA sequencing (FIG. 9B). Similar dose and time response were observed in plasma samples from irradiated rhesus monkeys. Time- and dose-dependent decrease in miR-150 was observed following the critical dose of 2 Gy and a higher dose of 5.5 Gy (FIG. 9D). Significant change in miR-150 levels was also noted in animals that received 0.5 Gy TBI, although response was less dramatic in the acute stage, but increased at one week post XRT. In the WTLI and gut irradiation models, a partial depletion in miR-150 was noted, however the level returned to baseline in 3 weeks, suggesting that it is an indicator of bone marrow damage and/or recovery (FIG. 10).

Figures 11D, 11E:
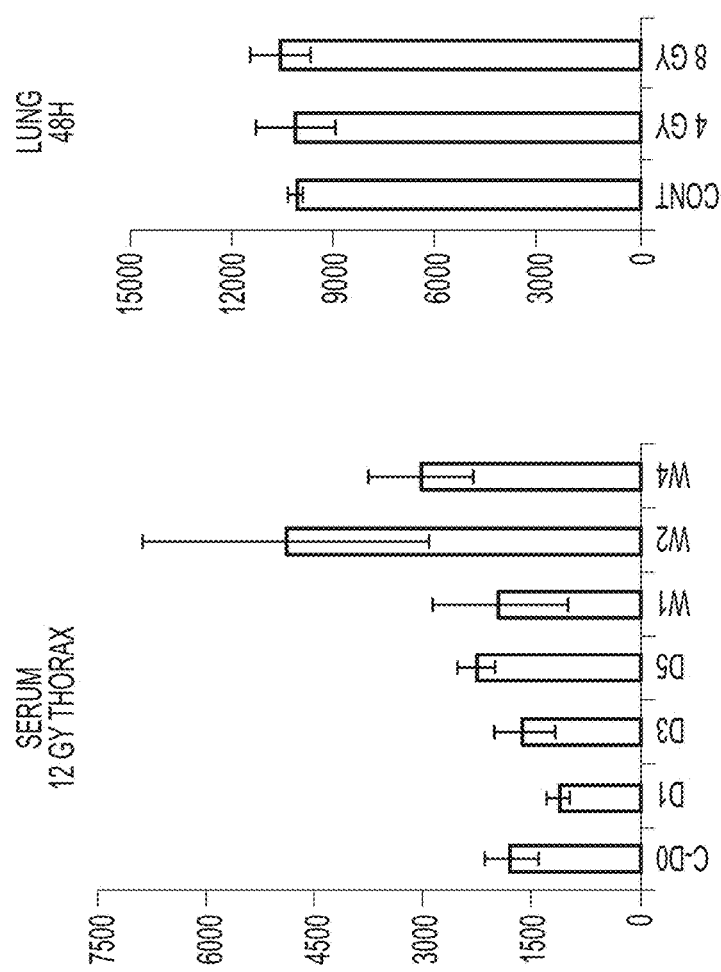

Identification of Biomarkers Connected with Organ-Specific Responses to XRT:

There are over 2000 miRNAs in mammalian cells and each cell type has a distinct signature with regard to their expression and abundance. For example miR-451, miR-142-3p, miR-223, etc. are high in bone marrow and blood cells, while miR-126 and let7 family, miR-29a and others are abundant in lung. HE system and lung constantly release exosomes with their respective signatures. Changes in serum miRNAs with distinct signature and kinetics were observed after WTLI. For example, increases in miR-21 and miR-29a were observed 2 weeks after WTLI, a time point where inflammation and active release of exosomes or leaking are predicted [Rube, C. E., et al. (2000) Int J Radiat Oncol Biol Phys 47(4):1033-42]. Several of the markers that peaked in the serum at 2 weeks were found to be very abundant in lung (FIG. 11, Table 1). Organ specificity was confirmed with parallel analysis failing to detect these miRs in serum samples collected from control animals or animals exposed to GI radiation (FIG. 11). Further, several of these miRs are reported to be altered in lung diseases, or are mechanistically connected to responses such as lung injury and/or inflammation [Hassan, F., et al. (2012) PLoS ONE 7(11):e50837; Izzotti, A., et al. (2009) Faseb J 23(3):806-12; Oglesby, I. K., et al. (2010) J Immunol 184(4):1702-9]. Delayed effects of radiation, such as pneumonitis, were evident from microCT and MM analysis at around 20 weeks after radiation in several animals (data not shown). Dose effects were evident from the differences in serum markers, latency and incidence of delayed effects, when compared 8 Gy vs 12 Gy exposed animals. Overall, data from organ targeted/protected irradiation animals led to the development of a panel of miRNA biomarkers that provide references for evaluating organ responses after partial body exposure.

TABLE 1 miRNA markers with distinct response with potential connection with organ function, along with several controls.

| Organ | Response/Connection | Serum/Plasma miRs identified |
|---|---|---|
| Lung | | |
| 1-3 days | Tissue/DNA damage/ Apoptosis/systemic response | miR-200b, miR-191-5p, miR-144-3p, miR-142-3p, miR-192 |
| 2 weeks | Inflammatory response/ Lung injury/leakage | miR-21, miR-29a, miR-126-3p, let-7c, miR-191-5p, miR-15b, miR-130a, miR-19a |
| 8+ weeks | Pneumonitis/progression/ systemic effects | miR-146a, miR-486, miR-25, miR-192 |
| HE | HE stem cells depletion/ recovery | miR-150 |
| GI | TLR signaling | miR-574-5p (6-10 fold increase in NHPs, 5.5 Gy 24 h) |
| Controls | Hemolysis | miR-451, miR-16, miR-106b |
| | Internal Controls | miR-30a, miR-23a, miR130b |
| | Cellular RNA contamination | Actin, Tubulin, Gapdh, Rpl19 |
| | Normalizers (spike-ins) | At-159a, Cel-248, Osa-414 |

Example 3: Diagnosis of Radiation Induced Lung Injury, Pneumonitis, and Lung Fibrosis BALB/c mice received 12 Gy whole thorax lung irradiation (WTLI), resulting in pneumonitis and death at 20-22 weeks. Rhesus monkeys received 9 Gy or 11.5 Gy WTLI. The 11.5 Gy animals were euthanized due to pneumonitis at 79-162 days. Serum/Plasma was collected at C-D1, D1, D3, D5, Wk1, Wk2, Wk4, Wk8, Wk12, and C-12 Wk for mice; and D0, D1/2, D5, and D8 for monkeys.

Figure 12:
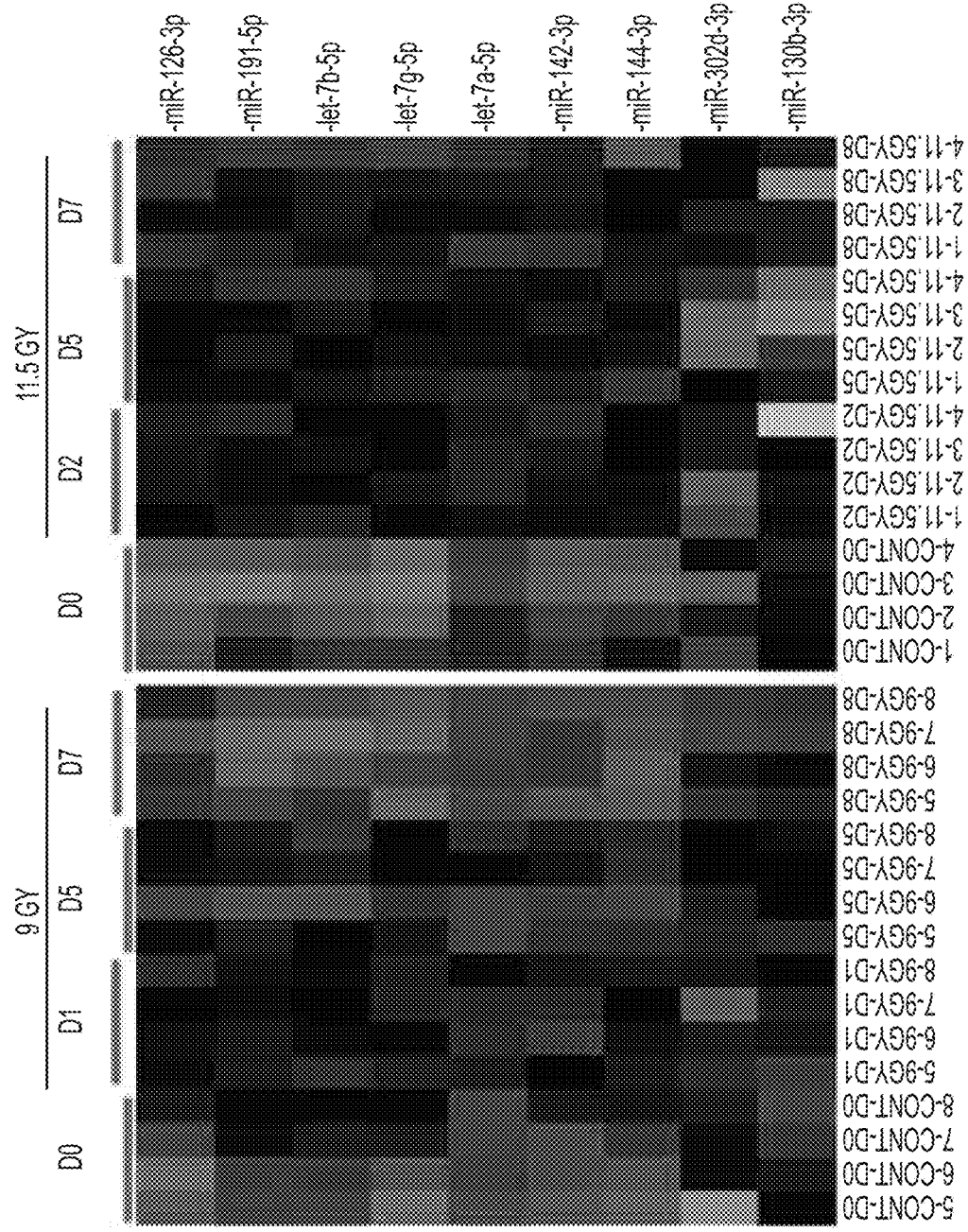
FIG. 12 is a heatmap showing results of 6 marker panel (and 2 controls) for plasma collected from rhesus monkeys that received 9 Gy or 11.5 Gy whole thorax irradiation (WTI).

FIG. 12 is a heatmap showing results of 6 marker panel (and 2 controls) for the rhesus monkey-WTLI model.

Figure 13A:
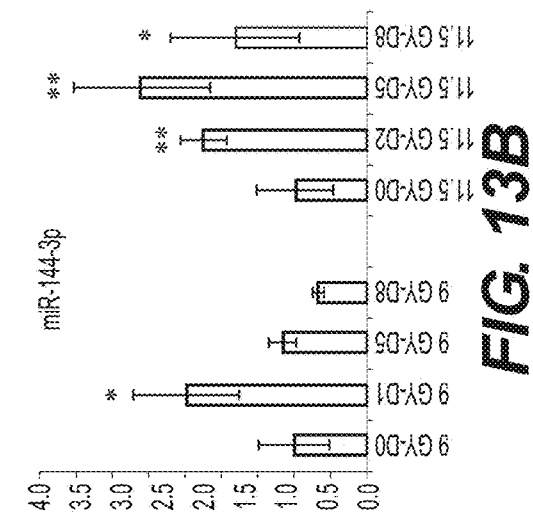
FIGS. 13A to 13C are bar graphs showing miR-191-5p (FIG. 13A), miR-144-3p (FIG. 13B), and miR-302-3p (FIG. 13C) expression as a function of WTI dose and time.
Figure 13B:
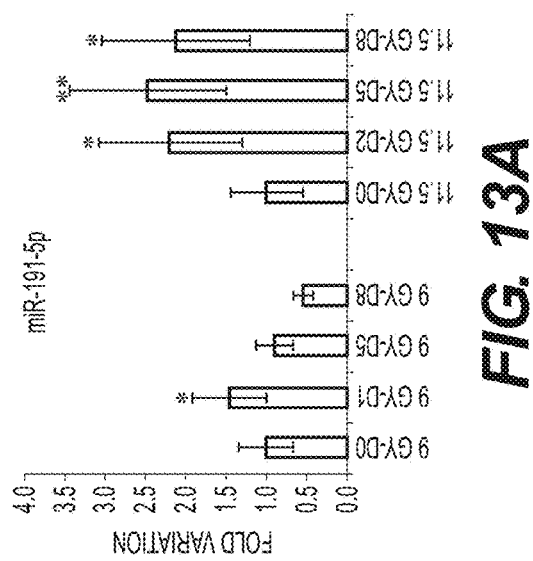
Figure 13C:
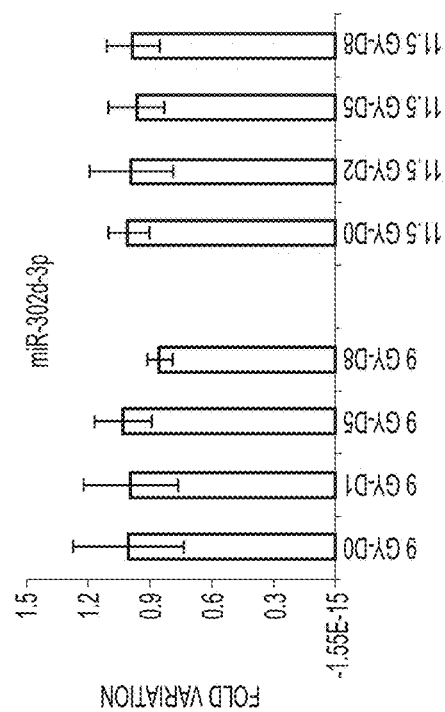

FIGS. 13A to 13C are bar graphs showing miR-191-5p (FIG. 13A), miR-144-3p (FIG. 13B), and miR-302-3p (FIG. 13C) expression as a function of WTLI dose and time. miR-191-5p is upregulated in lung exposed to cigarette smoke (targets Nrf2). miR-144-3p is altered in idiopathic pulmonary fibrosis (IPF), cystic fibrosis (CF), etc., and targets CFTR gene. miR-302-3p was used as an internal control.

Figure 14A:
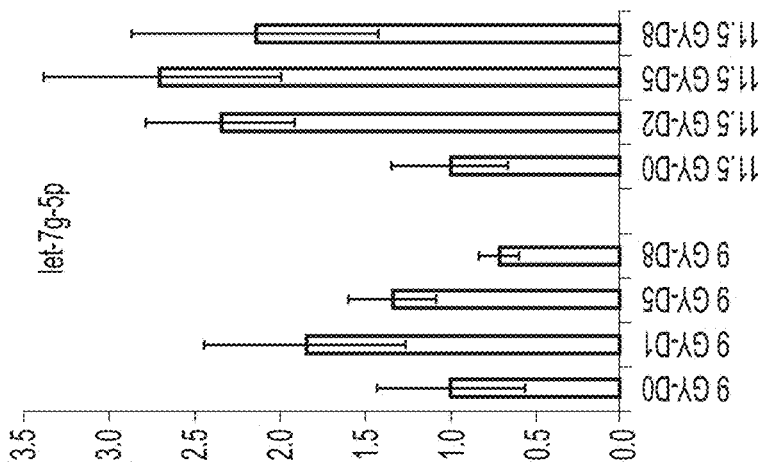
FIGS. 14A to 14C are bar graphs showing miR-142-3p (FIG. 14A), miR-126-3p (FIG. 14B), and let-7g-5p (FIG. 14C) expression as a function of WTI dose and time.
Figure 14B:
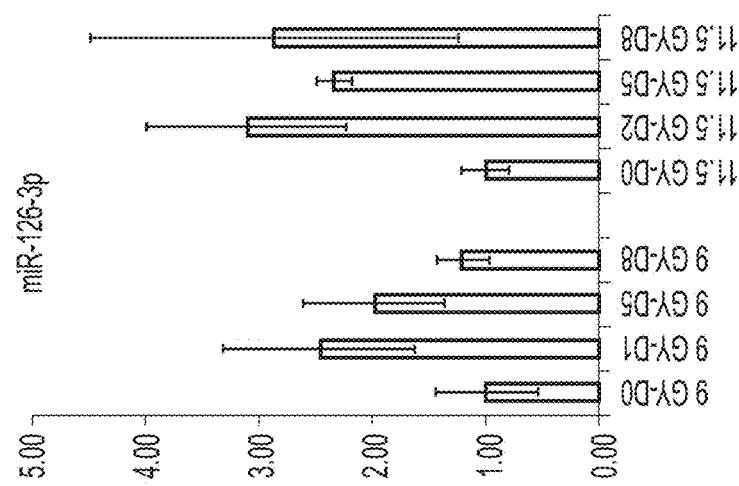
Figure 14C:
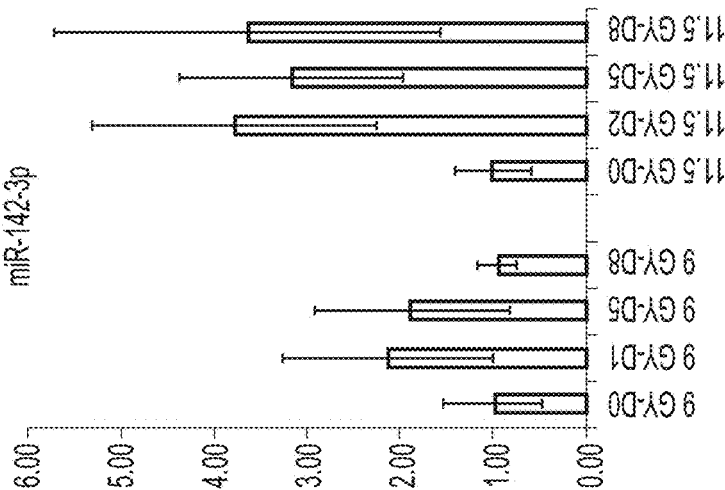

FIGS. 14A to 14C are bar graphs showing miR-142-3p (FIG. 14A), miR-126-3p (FIG. 14B), and let-7g-5p (FIG. 14C) expression as a function of WTLI dose and time. miR-142-3p regulate innate immune response functional regulation of IL-6 in dendritic cells. miR-126-3p expression is down in CF airway epithelial cells, and regulates innate immune response. let7 family abundant in lung and implicated in lung diseases.

Figures 15C, 15D:
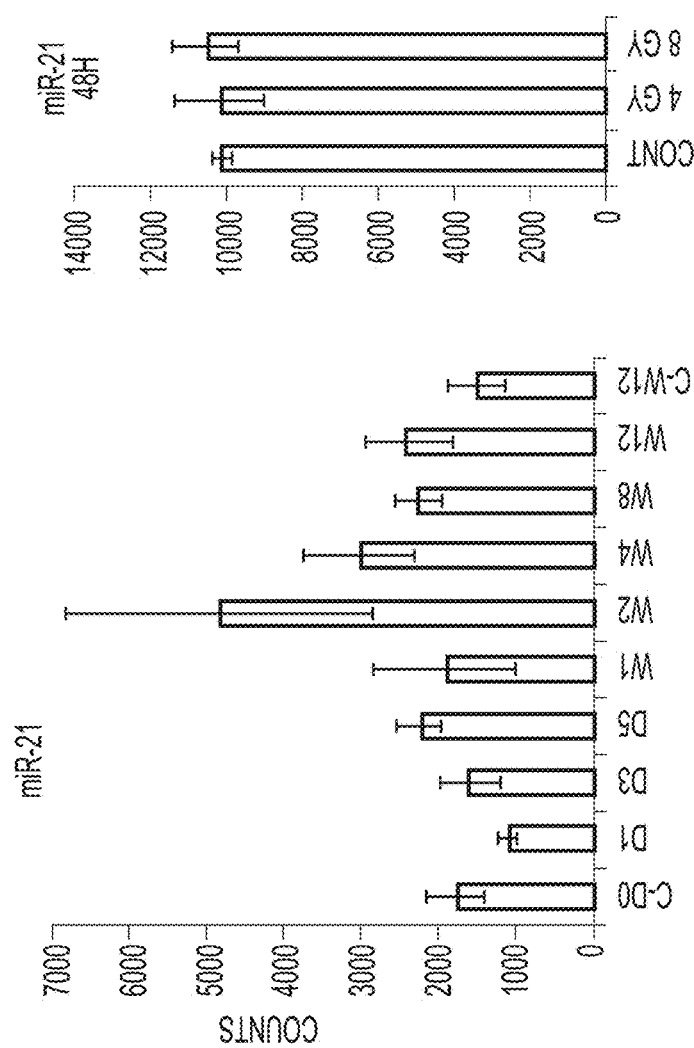
FIGS. 15A to 15N are bar graphs showing serum (FIGS. 15A, 15C, 15E, 15G, 15I, 15K, 15M) and lung (FIGS. 15B, 15D, 15F, 15H, 15J, 15L, 15N) levels of miR-150 (FIGS. 15A, 15B), miR-21 (FIGS. 15C, 15D), miR-200b (FIGS. 15E, 15F), miR-29a (FIGS. 15G, 15H), miR-146a (FIGS. 15I, 15J), miR-126-3p (FIGS. 15K, 15L), and miR-192 (FIGS. 15M, 15N) after WTI.
FIG. 15O shows serum levels of miR-192 after gut irradiation.
Figures 15E, 15F:
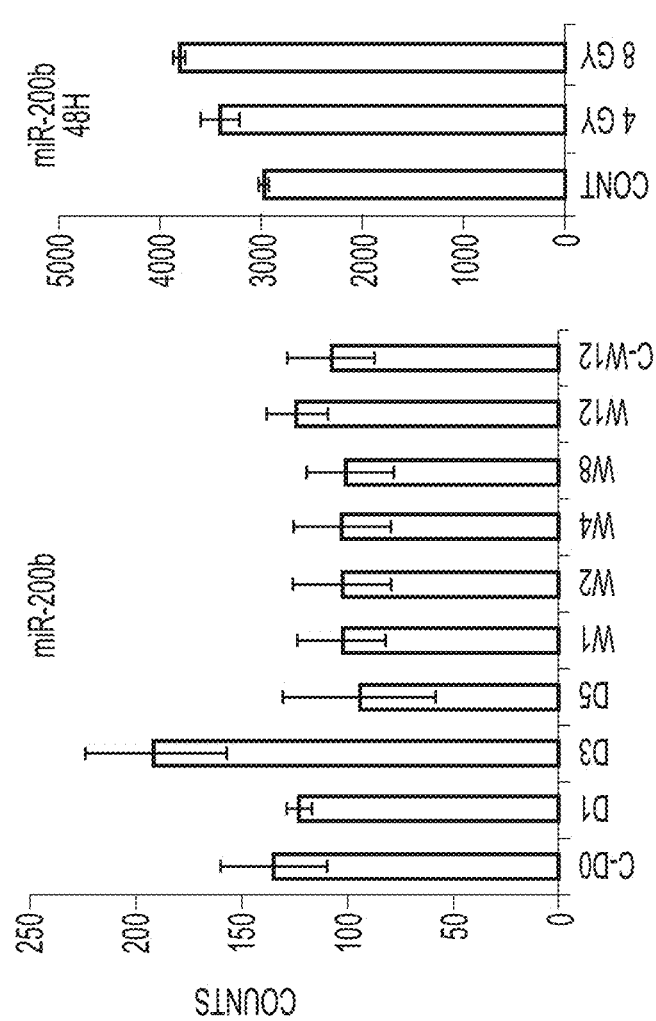
Figures 15G, 15H:
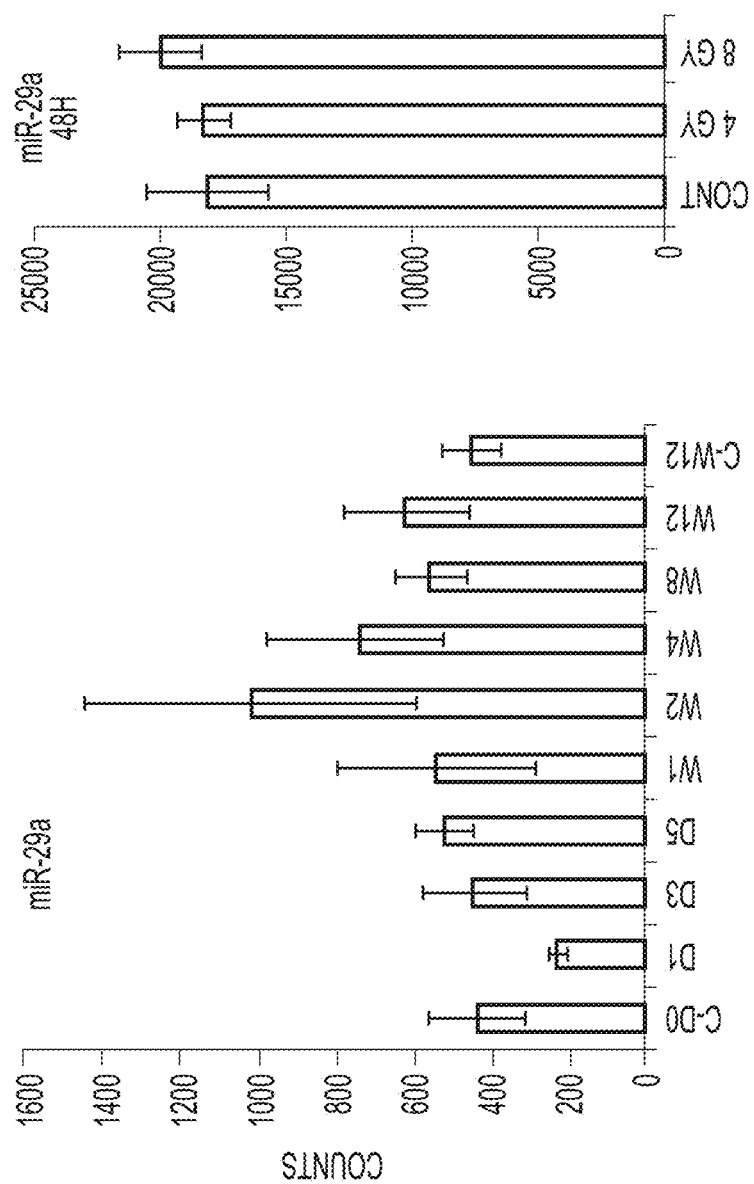

FIGS. 15A to 15X are bar graphs showing serum (FIGS. 15A, 15C, 15E, 15G, 15I, 15K, 15M) and lung (FIGS. 15B, 15D, 15F, 15H, 15J, 15L, 15N) levels of miR-150 (FIGS. 15A, 15B), miR-21 (FIGS. 15C, 15D), miR-200b (FIGS. 15E, 15F), miR-29a (FIGS. 15G, 15H), miR-146a (FIGS. 15I, 15J), miR-126-3p (FIGS. 15K, 15L), and miR-192 (FIGS. 15M, 15N) after WTI. FIG. 15O shows serum levels of miR-192 after gut irradiation.

Table 1 shows circulating miRNAs that are indicators of lung injury and are predictors of delayed and late effects.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for measuring exposure of a human subject to ionizing radiation and administering a treatment method according to results thereof, comprising
    (a) assaying a blood sample from a human subject exposed to radiation to measure the levels of miR-150, wherein the blood sample comprises whole blood, serum or plasma;
    (b) assaying the sample to measure the levels of miR-23a;
    (c) normalizing the miR-150 levels based specifically on the miR-23a levels;
    (d) estimating the measure of ionizing radiation exposure from the normalized miR-150 levels;
    (e) identifying a human subject exposed to a remediable level of radiation poisoning, and
    (f) administering to the human subject exposed to a remediable dose of radiation poisoning an immune modulator or mitigator according to level of radiation exposure.

2. The method of claim 1, wherein the levels of miR150 are a measure of absorbed radiation dose and evaluation of hematologic effects from ionizing radiation exposure.

3. The method of claim 1, further comprising assaying the sample to measure the levels of miR-16 whose presence in the sample is an indication of hemolysis contamination, wherein hemolysis contamination is an indication that the sample should be discarded.

4. The method of claim 1, further comprising spiking the sample with known amounts of at least one oligonucleotide, and determining in the sample levels of the at least oligonucleotide to further normalize the miR-150 levels.

5. The method of claim 1, further comprising assaying the sample to measure the levels of miRNA-25 whose presence in the sample is an indication of hemolysis contamination, wherein hemolysis contamination is an indication that the sample should be discarded.

6. The method of claim 1, further comprising assaying the sample to measure the levels of miRNA-93 whose presence in the sample is an indication of hemolysis contamination, wherein hemolysis contamination is an indication that the sample should be discarded.

7. The method of claim 1, further comprising assaying the sample to measure the levels of miRNA-106b whose presence in the sample is an indication of hemolysis contamination, wherein hemolysis contamination is an indication that the sample should be discarded.

8. The method of claim 1, further comprising assaying the sample to measure the levels of miR-451 whose presence in the sample is an indication of hemolysis contamination, wherein hemolysis contamination is an indication that the sample should be discarded.

9. The method of claim 1, wherein the immune modulator or mitigator is a hematopoietic stem cell transplant, antibiotic, a blood transfusion, or administration of growth factors.

10. The method of claim 1, wherein the growth factor is GM-CSF.

* * * * *

UNITED STATES PATENT AND TRADEMARK OFFICE
CERTIFICATE OF CORRECTION

PATENT NO. : 10,407,726 B2
APPLICATION NO. : 15/846962
DATED : September 10, 2019
INVENTOR(S) : Naduparambil Jacob et al.

Page 1 of 1

It is certified that error appears in the above-identified patent and that said Letters Patent is hereby corrected as shown below:

In the Specification

Column 1, Lines 16-19, regarding Federally sponsored research. The statement, which reads, "This invention was made with Government Support under Grant No. U19AI067798-09 awarded by the National Institutes of Health. The Government has certain rights in the invention."

Should read --This invention was made with government support under grant/contract number W81XWH-15-2-0054 awarded by the ARMY/MRMC. The government has certain rights in the invention.--

Signed and Sealed this
Eleventh Day of October, 2022

Katherine Kelly Vidal
*Director of the United States Patent and Trademark Office*